(12) United States Patent
Wood et al.

(10) Patent No.: US 10,011,577 B2
(45) Date of Patent: Jul. 3, 2018

(54) METHODS FOR PRODUCING 5-(HALOMETHYL)FURFURAL

(71) Applicant: MICROMIDAS, INC., West Sacramento, CA (US)

(72) Inventors: Alex B. Wood, Sacramento, CA (US); Makoto N. Masuno, Elk Grove, CA (US); Ryan L. Smith, Sacramento, CA (US); John Bissell, Sacramento, CA (US); Dimitri A. Hirsch-Weil, Sacramento, CA (US); Robert Joseph Araiza, Sacramento, CA (US); Daniel R. Henton, Midland, MI (US); James H. Plonka, Midland, MI (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 15/022,882

(22) PCT Filed: Sep. 19, 2014

(86) PCT No.: PCT/US2014/056572
§ 371 (c)(1),
(2) Date: Mar. 17, 2016

(87) PCT Pub. No.: WO2015/042407
PCT Pub. Date: Mar. 26, 2015

(65) Prior Publication Data
US 2016/0207897 A1 Jul. 21, 2016

Related U.S. Application Data

(60) Provisional application No. 61/880,751, filed on Sep. 20, 2013, provisional application No. 62/002,714, filed on May 23, 2014.

(51) Int. Cl.
*C07D 307/46* (2006.01)
*C07D 307/50* (2006.01)
*B01J 27/10* (2006.01)

(52) U.S. Cl.
CPC .......... *C07D 307/46* (2013.01); *B01J 27/10* (2013.01); *C07D 307/50* (2013.01)

(58) Field of Classification Search
None
See application file for complete search history.

(56) References Cited

U.S. PATENT DOCUMENTS

| | | | |
|---|---|---|---|
| 2,494,325 A | 1/1950 | Anne et al. | |
| 2,611,740 A | 9/1952 | Berriman et al. | |
| 4,001,283 A | 1/1977 | Wells, Jr. | |
| 4,424,390 A | 1/1984 | Hamada et al. | |
| 4,433,155 A | 2/1984 | Gilpin | |
| 4,971,657 A | 11/1990 | Avignon et al. | |
| 6,162,350 A | 12/2000 | Soled et al. | |
| 6,788,280 B2 | 9/2004 | Ham | |
| 7,173,142 B2 | 2/2007 | Steiner et al. | |
| 7,829,732 B2 * | 11/2010 | Mascal ............... | C07D 307/48 549/483 |
| 9,102,644 B2 | 8/2015 | Mikochik et al. | |
| 9,126,964 B2 | 9/2015 | Masuno et al. | |
| 9,388,150 B2 | 7/2016 | Kim et al. | |
| 9,388,151 B2 | 7/2016 | Browning et al. | |
| 9,586,922 B2 | 3/2017 | Wood et al. | |
| 9,637,463 B2 | 5/2017 | Masuno et al. | |
| 9,718,798 B2 | 8/2017 | Browning et al. | |
| 2005/0032707 A1 | 2/2005 | Prasad et al. | |
| 2007/0161795 A1 | 7/2007 | Cvak et al. | |
| 2009/0234142 A1 | 9/2009 | Mascal | |
| 2010/0083565 A1 | 4/2010 | Gruter | |
| 2010/0210745 A1 | 8/2010 | McDaniel et al. | |
| 2011/0144359 A1 | 6/2011 | Heide et al. | |
| 2014/0066641 A1 | 3/2014 | Cho et al. | |
| 2014/0100378 A1 | 4/2014 | Masuno et al. | |
| 2014/0187802 A1 | 7/2014 | Mikochik et al. | |
| 2015/0203462 A1 | 7/2015 | Cahana et al. | |
| 2015/0266843 A1 | 9/2015 | Browning et al. | |
| 2016/0002190 A1 | 1/2016 | Browning et al. | |
| 2016/0002191 A1 | 1/2016 | Wood et al. | |
| 2016/0168107 A1 | 6/2016 | Masuno et al. | |
| 2017/0137397 A1 | 5/2017 | Wood et al. | |

FOREIGN PATENT DOCUMENTS

| | | |
|---|---|---|
| CN | 1190979 A | 8/1998 |
| CN | 1281424 A | 1/2001 |
| CN | 101475544 A | 7/2009 |
| CN | 102066304 A | 5/2011 |

(Continued)

OTHER PUBLICATIONS

"Database WPI Week 200952", XP002684874, retrieved on Oct. 12, 2012, 4 pages.
Intention to Grant received for European Patent Application No. 12733249.2, dated Mar. 30, 2015, 7 pages.
Intention to Grant received for European Patent Application No. 12733249.2, dated Aug. 21, 2015, 7 pages.
Non Final Office Action received for U.S. Appl. No. 14/124,240, dated Aug. 14, 2014, 13 pages.
Non Final Office Action received for U.S. Appl. No. 14/124,240, dated Nov. 14, 2014, 13 pages.
Notice of Allowance received for U.S. Appl. No. 14/124,240, dated Apr. 10, 2015, 7 pages.
Notice of Allowance received for U.S. Appl. No. 14/438,600, dated Nov. 12, 2015, 6 Pages.
Notice of Allowance received for U.S. Appl. No. 14/438,600, dated Mar. 14, 2016, 5 pages.

(Continued)

*Primary Examiner* — Heidi Reese
(74) *Attorney, Agent, or Firm* — Morrison & Foerster LLP

(57) ABSTRACT

The present disclosure provides methods to produce 5-(halomethyl)furfural, including 5-(chloromethyl)furfural, by acid-catalyzed conversion of C6 saccharides, including isomers thereof, polymers thereof, and certain derivatives thereof. The methods make use of acids with lower concentrations, and allows for conversion of sugars into 5-(halomethyl)furfural at higher temperatures and faster reaction or residence times.

35 Claims, 3 Drawing Sheets

(56) References Cited

FOREIGN PATENT DOCUMENTS

| | | |
|---|---|---|
| CN | 102675265 A | 9/2012 |
| CN | 103930411 A | 7/2014 |
| CN | 104955817 A | 9/2015 |
| DE | 635783 C | 9/1936 |
| EP | 0079206 A1 | 5/1983 |
| EP | 0291494 A2 | 11/1988 |
| EP | 1049657 B1 | 3/2003 |
| FR | 2285386 A1 | 4/1976 |
| GB | 1220851 A | 1/1971 |
| GB | 1448489 A | 9/1976 |
| JP | 58-79988 A | 5/1983 |
| RU | 2429234 C2 | 9/2011 |
| WO | 1996/038500 A1 | 12/1996 |
| WO | 1999/025675 A1 | 5/1999 |
| WO | 2009/155297 A1 | 12/2009 |
| WO | 2011/161141 A1 | 12/2011 |
| WO | 2012/111988 A1 | 8/2012 |
| WO | 2012/170520 A1 | 12/2012 |
| WO | 2013/024162 A1 | 2/2013 |
| WO | 2014/066746 A1 | 5/2014 |
| WO | 2014/159741 A1 | 10/2014 |
| WO | 2015/023918 A2 | 2/2015 |

OTHER PUBLICATIONS

Office Action Received for Chinese Patent Application No. 201280028270.2, dated Jan. 23, 2015, 11 pages (7 pages of English Translation and 4 pages of Official Copy).
Office Action received for Chinese Patent Application No. 201280028270.2, dated Oct. 10, 2015, 6 pages (3 pages of English Translation and 3 pages of Official Copy).
Aho et al., "Catalytic Pyrolysis of Biomass in a Fluidized Bed Reactor: Influence of the Acidity of H-Beta Zeolite", Trans ICheme, Part B, Process Safety and Environmental Protection, vol. 85, No. B5, Sep. 2007, pp. 473-480.
Aho et al., "Catalytic Upgrading of Woody Biomass Derived Pyrolysis Vapours Over Iron Modified Zeolites in a Dual-Fluidized Bed Reactor", Fuel, vol. 89, 2010, pp. 1992-2000.
Brasholz et al., "Highly Efficient Dehydration of Carbohydrates to 5-(chloromethyl)Furfural(CMF), 5-(hydroxymethyl)Furfural (HMF) and Levulinic acid by Biphasic Continuous Flow Processing", Green Chemistry, vol. 13, 2011, pp. 1114-1117.
Breeden et al., "Microwave Heating for Rapid Conversion of Sugars and Polysaccharides to 5-Chloromethyl Furfural", Green Chemistry, vol. 15, 2013, pp. 72-75.
Chheda et al., "Production of 5-Hydroxymethylfurfural and Furfural by Dehydration of Biomass-Derived Mono- and Poly-Saccharides", Royal Society of Chemistry, Green Chemistry, vol. 9, 2007, pp. 342-350.
Chundury et al., "Preparation of Polymeric Building Blocks from 5-Hydroxymethyl- and 5-Chloromethylfurfuraldehyde", Industrial and Engineering Chemistry Product Research and Development, vol. 20, No. 1, 1981, pp. 158-163.
Dunlop, A. P., "Furfural Formation and Behavior", Industrial & Engineering Chemistry, vol. 40, No. 2, 1948, pp. 204-209.
Fenton et al., "XLI.—Bromomethylfurfuraldehyde", Journal of the Chemical Society, Transactions, vol. 75, 1899, pp. 423-433.
Haworth et al., "The Conversion of Sucrose into Furan Compounds. Part I. 5-Hydroxymethylfurfuraldehyde and some derivatives", Journal of the Chemical Society, 1944, pp. 667-670.
Kumari et al., "Synthesis of 5-Bromomethylfurfural from Cellulose as a Potential Intermediate for Biofuel", European Journal of Organic Chemistry, vol. 2011, 2011, pp. 1266-1270.
Liley, Peter E., "Section 2: physical and chemical data", Perry's chemical engineer's handbook, 1997, 1 page.
Liu et al., "Theoretical Studies on Thermochemistry for Conversion of 5-Chloromethylfurfural into Valuable Chemicals", The Journal of Physical Chemistry A, vol. 115, No. 46, 2011, pp. 13628-13641.
Mascal et al., "Towards the Efficient, Total Glycan Utilization of Biomass", Chemsuschem, vol. 2, 2009, pp. 423-426.
Mascal, M. , "Direct, High-Yield Conversion of Cellulose into Biofuel", Angewandte Chemie International Edition, vol. 120, 2008, pp. 8042-8044.
Mascal et al., "Dramatic Advancements in the Saccharide to 5-(Chloromethyl)furfural Conversion Reaction", Chemsuschem, vol. 2, No. 9, Sep. 21, 2009, pp. 859-861.
Nawale et al., "Synthesis and Evaluation of Novel Thiazolidinedione Derivatives for Antibacterial Activity", Der Pharma Chemica, vol. 4, No. 6, 2012, pp. 2270-2277.
Szmant et al., "The preparation of 5-chloromethylfurfuraldehyde from high fructose corn syrup and other carbohydrates", Journal of Chemical Technology and Biotechnology, vol. 31, No. 1, 1981, pp. 205-212.
International Preliminary Report on Patentability received for PCT Patent Application No. PCT/US2012/041087, dated Dec. 27, 2013, 8 pages.
International Search Report and Written Opinion received for PCT Patent Application No. PCT/US2012/041087, dated Oct. 19, 2012, 12 pages.
International Preliminary Report on Patentability received for PCT Patent Application No. PCT/US2013/066788, dated May 7, 2015, 9 pages.
International Search Report and Written Opinion received for PCT Patent Application No. PCT/US2013/066788, dated Feb. 6, 2014, 11 pages.
International Search Report and Written Opinion received for PCT Patent Application No. PCT/US2014/024940, dated Jul. 14, 2014, 12 pages.
International Search Report and Written Opinion received for PCT Patent Application No. PCT/US2014/024949, dated Jul. 11, 2014, 17 pages.
International Preliminary Report on Patentability received for PCT Patent Application No. PCT/US2014/024949, dated Sep. 24, 2015, 15 pages.
International Search Report & Written Opinion received for PCT Patent Application No. PCT/US2014/056572, dated Nov. 24, 2014, 9 pages.
International Preliminary Report on Patentability received for PCT Patent Application No. PCT/US2014/024940, dated Oct. 1, 2015, 9 pages.
International Preliminary Report on Patentability received for PCT Patent Application No. PCT/US2014/056572, dated Mar. 31, 2016, 7 pages.
Werther, Joachim, "Fluidized-Bed Reactors", Wiley Online Library, Ullmann's Encyclopedia of Industrial Chemistry, 2007, 48 pages.
Wikipedia, "1,2-dichloroethane", Available online at <http://en.wikipedia.org/wiki/1,2-Dichloroethane> on Aug. 3, 2014, 4 pages.
Worden, Edward Chauncey, "Technology of Cellulose Esters", vol. 1, Part 1, 1921, p. 186.
Fenton et al., "LXXV-Derivatives of Methylfurfural", Journal of the Chemical Society, Transactions, vol. 79, 1901, pp. 807-816.
Moye, C. J., "5-Hydroxymethylfurfural", Reviews of Pure and Applied Chemistry, vol. 14, Jan. 1964, pp. 161-170.
Sanda et al., "The Vilsmeier Reaction: A New Synthetic Method for 5-(Chloromethyl)-2-furaldehyde", Synthesis, No. 6, 1992, pp. 541-542.
Surh et al., "5-Sulfooxymethylfurfural as a possible ultimate Mutagenic and Carcinogenic Metabolite of the Maillard reaction Product, 5-Hydroxymethylfurfural", Carcinogenesis, vol. 15, No. 10, 1994, pp. 2375-2377.
Surh et al., "Activation of the Maillard Reaction Product 5-(Hydroxymethyl) Furfural to Strong Mutagens via Allylic Sulfonation and Chlorination", Chemical Research in Toxicology, vol. 7, 1994, pp. 313-318.
Timko et al., "The Furanyl Unit in Host Compounds", Journal of the American Chemical Society, vol. 96, No. 22, 1974, pp. 7159-7160.
Quiroz-Florentino et al., "Total Synthesis of Naturally Occurring Furan Compounds 5-{[(4-Hydroxybenzyl)oxy]methyl}-2-Furaldehyde and Pichiafuran C", Synthesis, vol. 7, 2011, pp. 1106-1112.

(56) References Cited

OTHER PUBLICATIONS

Hibbert et al., "Studies on Cellulose Chemistry II The Action of dry Hydrogen Bromide on Carbohydrates and Polysaccharides", Journal of the American Chemical Society, vol. 45, No. 1, 1923, pp. 176-182.
Extended European Search Report (includes Supplementary European Search Report and Search Opinion) received for European Patent Application No. 14776137.3, dated Jul. 4, 2016, 5 pages.
Extended European Search Report received for European Patent Application No. 14773258.0, dated Oct. 19, 2016, 6 Pages.
International Search Report and Written Opinion received for PCT Patent Application No. PCT/US2016/022790, dated Jun. 3, 2016, 8 Pages.
Non-Final Office Action received for U.S. Appl. No. 14/852,152 dated Nov. 23, 2016, 7 pages.
Non-Final Office Action received for U.S. Appl. No. 14/805,321, dated Aug. 11, 2016, 12 pages.
Notice of Allowance received for U.S. Appl. No. 14/852,306, dated Oct. 26, 2016, 13 pages.
Notice of Allowance received for U.S. Appl. No. 14/805,321, dated Dec. 29, 2016, 7 pages.
Alonso et al., "Catalytic Conversion of Biomass to Biofuels", Green Chemistry, vol. 12, 2010, pp. 1493-1513.
Bemiller, James N., "Carbohydrates", Kirk-Othmer Encyclopedia of Chemical Technology, vol. 4, Jan. 16, 2004, pp. 696-733.
Hamada et al., "An Improved Method for the Conversion of Saccharides into Furfural Derivative", Chemistry Letters, The Chemical Society of Japan, 1982, pp. 617-618.
Jin et al., "Application of Hydrothermal Reaction to Conversion of Plant-Origin Biomasses into Acetic and Lactic Acids", Journal of Materials Science, vol. 43, 2008, pp. 2463-2471.
Kaliyan et al., "Densification Characteristics of Corn Cobs", Fuel Processing Technology, vol. 91, 2010, pp. 559-565.
Zheng, Baohui, "Synthesis of Sucrose Derivatives and Catalytic Reaction Process", Thesis for Ph.D of Nanjing University of Science and Technology, Jul. 2012, pp. 62-63 (with 4 pages of English Translation).
DDBST GMBH, "Saturated Vapor Pressure Chart: Chloroform", Available Online at <http://ddbonline.ddbst.com/DDBSearch/onlineddboverview.exe>, Retrieved on Jan. 17, 2018, pp. 1-2.
Dhepe et al., "Cellulose Conversion under Heterogeneous Catalysis", ChemSusChem, vol. 1, 2008, pp. 969-975.
Extended European Search Report includes (Supplementary European Search Report and European Search Opinion) received for European Patent Application No. 14845176.8, dated Feb. 3, 2017, 8 pages.
Fenton et al., "CXLVIII.—Homologues of Furfuraldehyde", Journal of the Chemical Society, vol. 95, 1909, pp. 1334-1340.
Fine et al., "The Role of Moisture in the Corrosion of HBr Gas Distribution Systems", Journal of The Electrochemical Society, vol. 142, No. 4, Apr. 1995, pp. 1286-1293.
International Preliminary Report on Patentability received for PCT Patent Application No. PCT/US2016/022790, dated Sep. 28, 2017, 6 pages.
Mann, Uzi, "Reactor Technology", Kirk-Othmer Encyclopedia of Chemical Technology, vol. 21, 2006, pp. 1-36.
Non Final Office Action received for U.S. Appl. No. 15/468,728, dated Nov. 22. 2017, 11 pages.
Notice of Allowance received for U.S. Appl. No. 14/852,152, dated Mar. 24, 2017, 10 pages.
Notice of Allowance received for U.S. Appl. No. 15/418,385, dated Oct. 19, 2017, 11 pages.
Prior, Michael, "Size Reduction", Kirk-Othmer Encyclopedia of Chemical Technology, 2000, pp. 1-18.
Radel et al., "Brominations of Some 1,2,4-Triazine 2-Oxides", The Journal of Organic Chemistry, vol. 43, No. 12, 1978, pp. 2514-2517.

\* cited by examiner

METHODS FOR PRODUCING 5-(HALOMETHYL)FURFURAL

CROSS-REFERENCE TO RELATED APPLICATIONS

This application is a U.S. National Phase patent application of PCT/US2014/056572, filed Sep. 19, 2014, which claims the benefit of U.S. Provisional Patent Application Serial Nos. 61/880,751, filed Sep. 20, 2013 and 62/002,714, filed May 23, 2014, the disclosures of which are hereby incorporated herein by reference in their entireties.

FIELD

The present disclosure relates generally to the production of furfurals, and more specifically to the production of 5-(halomethyl)furfural, including, for example, 5-(chloromethyl)furfural or 5-(bromomethyl)furfural, from renewable biomass resources (e.g., cellulose, hemicellulose, starch, and sugar).

BACKGROUND

Efforts to reduce dependence on fossil fuels for transportation fuel and as feedstock for industrial chemicals have been undertaken for decades, with a particular focus on enabling economic feasibility of renewable feedstocks. Heightened efforts are being made to more effectively utilize renewable resources and develop "green" technologies, due to continued long-term increases in the price of fuel, increased environmental concerns, continued issues of geopolitical stability, and renewed concerns for the ultimate depletion of fossil fuels.

Cellulose in biomass is commonly used as a feedstock for biofuel production. For example, cellulose can be used to produce ethanol. Cellulose can also be used to produce furan-based biofuels by way of 5-(halomethyl)furfural, such as 5-(chloromethyl)furfural (CMF). CMF can be converted into 5-(ethoxymethyl)furfural, a compound considered as a promising diesel fuel additive. Alternatively, CMF can also be converted into 5-methylfurfural, another compound considered as a promising a biofuel candidate.

The production of CMF from cellulose was first described in the early 1900s. Currently, various synthetic routes are known in the art to produce CMF from biomass using concentrated hydrochloric acid. For example, U.S. Pat. No. 7,829,732 describes a method of producing CMF from biomass using concentrated hydrochloric acid and 1,2-dichloroethane as a solvent. See also, Szmant & Chundury, *J. Chem. Tech. Biotechnol.* 1981, 31, 205-212; Liu et al., *J. Phys. Chem. A,* 2011, 115, 13628-13641. The use of concentrated hydrochloric acid, however, can present several challenges on a commercial scale. For example, use of concentrated hydrochloric acid can cause corrosion of the reactors.

Thus, what is needed in the art are commercially viable methods to produce 5-(halomethyl)furfural from biomass, using lower acid concentrations.

BRIEF SUMMARY

Provided herein are methods for producing 5-(halomethyl)furfural, including 5-(chloromethyl)furfural (CMF) and 5-(bromomethyl)furfural (BMF), using lower acid concentrations than what is currently known in the art. Lower acid concentrations can provide process advantages for the commercial production of 5-(halomethyl)furfural. For example, lower acid concentrations can reduce corrosion of the reactors.

In one aspect, provided is a method for producing 5-(halomethyl)furfural by:
 a) combining a feedstock, an aqueous acid, and a salt in a reaction vessel to form a reaction mixture, wherein: the aqueous acid is a halogen-containing acid; and the reaction mixture has a [$H^+$] less than 12 M; and
 b) converting at least a portion of the feedstock in the reaction mixture to produce 5-(halomethyl)furfural.

In other embodiments, the method further includes isolating the 5-(halomethyl)furfural from the reaction mixture.

In some aspects, provided is also a composition that includes: a feedstock; an aqueous acid; and a salt, wherein: the aqueous acid is a halogen-containing acid; and the composition has a [$H^+$] less than 12 M.

In certain embodiments of the methods and compositions descried herein, the aqueous acid is hydrochloric acid or hydrobromic acid. In one variation, the aqueous acid is HX, wherein X is halo.

In certain embodiments of the methods and compositions descried herein, the salt has a formula $A^{r+}(X^-)_r$, where $A^{r+}$ is a cation having charge r, wherein X is halo and $X^-$ is an anion. In some variations, [$X^-$] is [$Cl^-$] or [$Br^-$].

In some embodiments that can be combined with any of the methods and compositions described herein, the feedstock, aqueous acid and salt are further combined with a solvent.

In some embodiments of the methods and compositions descried herein, the feedstock is selected from the group consisting of corn stover, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinnings, slash, miscanthus, switchgrass, sorghum, bagasse, manure, wastewater biosolids, green waste, and food or feed processing residues, or any combinations thereof. In other embodiments, the feedstock comprises glucose, fructose, sucrose, starch, inulin, cellulose, hemicellulose, cellulosic oligomers, cellobiose, or any combinations thereof.

DESCRIPTION OF THE FIGURES

The present application can be understood by reference to the following description taken in conjunction with the accompanying figures.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Figure 1:
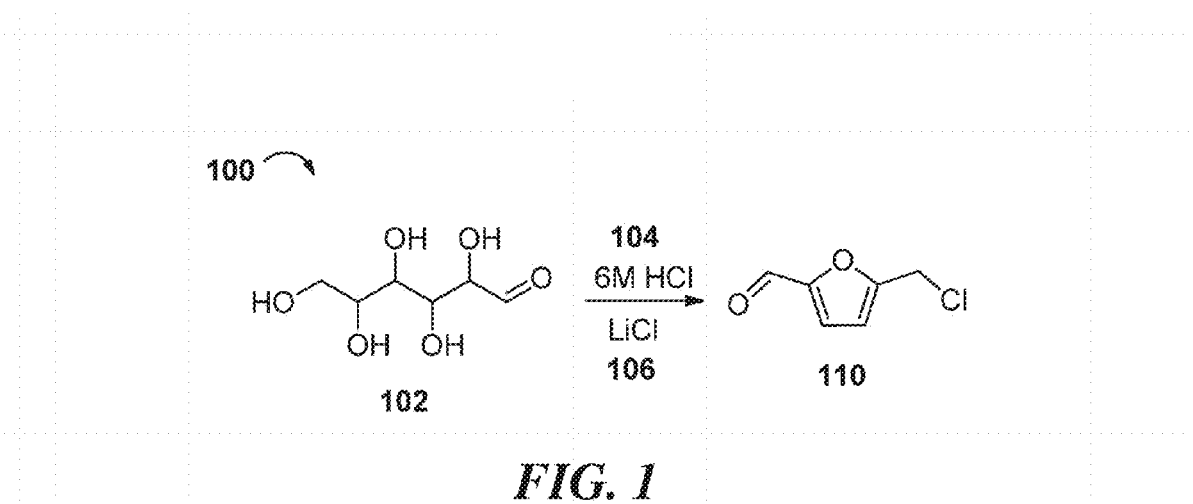
FIG. 1 depicts an exemplary reaction for converting glucose into 5-(chloromethyl)furfural using HCl and LiCl.

With reference to FIG. 1, method 100 is an exemplary reaction for producing 5-(halomethyl)furfural by contacting feedstock 102, acid 104, and salt 106. Feedstock 102 in this exemplary reaction is glucose. While the glucose is depicted in open-chain form in FIG. 1, it should be understood, however, any isomers of glucose may be used. For example, feedstock 102 may be a cyclic isomer of glucose. The open-chain form of glucose used in method 100 may exist in equilibrium with several cyclic isomers. Further, feedstock 102 may also be a monosaccharide (as depicted in FIG. 1), or in other variations, disaccharides or polysaccharides made up of monomeric units having six carbon atoms.

As depicted in FIG. 1, acid 104 is hydrochloric acid (HCl), thereby producing 5-(chloromethyl)furfural as product 110. It should be understood, however, hydrobromic acid may also be used to produce 5-(bromomethyl)furfural under similar reaction conditions as described for method 100. While hydrochloric acid is provided for use in method 100, it should also be understood that, in other exemplary embodiments, acid 104 may be generated in situ by combining reagents that may form acid 104 in situ in the reaction mixture.

The concentration of the acid used in method 100 is less than 12 M. As depicted in FIG. 1, acid 104 is 6 M hydrochloric acid. It should be understood, however, that the acid concentration may vary depending on various factors, including the type of feedstock used. For example, in other exemplary reactions, the feedstock may be fructose, and 4 M hydrochloric acid may be used.

Exemplary method 100 further requires the presence of a salt in the reaction mixture. Salt 106 as depicted in FIG. 1 is lithium chloride. It should be understood that other suitable salts may be used. For example, in another variation, the method may use calcium chloride, or a combination of lithium chloride and calcium chloride as the salt(s). It should also be understood that hydrobromic acid may be used to produce 5-(bromomethyl)furfural under similar reaction conditions as described for method 100. While lithium chloride is provided for use in method 100, it should also be understood that, in other exemplary embodiments, salt 106 may be generated in situ by combining reagents that may form salt 106 in the reaction mixture.

Exemplary method 100 is typically carried out at an elevated temperature. For example, method 100 may be carried out at a reaction temperature of at least 80° C.

It should be understood that method 100 may use one or more additional reagents. For example, in some variations, method 100 may include a solvent or mixture of solvents. Further, it should be understood that method 100 may employ one or more additional steps. For example, in other variations, method 100 may further include isolating the 5-(halomethyl)furfural from the reaction mixture.

The methods and compositions described herein employ various reagents and reaction conditions, each of which is described in further detail below.

Feedstocks

The feedstocks used in the methods described herein refer to the starting materials for such methods. Feedstocks suitable for producing 5-(halomethyl)furfural may include any materials that contain saccharides. In some embodiments, the feedstock may include six-carbon (C6) saccharides. It should be understood that "six-carbon saccharides" or "C6 saccharides" refers to saccharides where the monomeric unit has six carbons. The feedstock may include monosaccharides, disaccharides, polysaccharides, or any mixtures thereof. In one variation, the feedstock includes one or more C6 monosaccharides. In another variation, the feedstock is a disaccharide or polysaccharide comprising monomeric units having six carbon atoms. It should be understood that the monomeric units may the same or different.

In one embodiment, the feedstock is a monosaccharide. Examples of suitable monosaccharides include glucose, fructose, and any other isomers thereof. In another embodiment, the feedstock is a disaccharide. Examples of suitable disaccharides include sucrose. In yet another embodiment, the feedstock is a polysaccharide. Examples of polysaccharides include cellulose, hemicellulose, cellulose acetate, and chitin. In other embodiments, the feedstock includes a mixture of monosaccharides, disaccharides, polysaccharides. For example, in one variation, the feedstock may include glucose, sucrose and cellulose.

In some embodiments, the feedstock includes C6 saccharides selected from glucose, fructose (e.g., high fructose corn syrup), cellobiose, sucrose, lactose, and maltose, or isomers thereof (including any stereoisomers thereof), or any mixtures thereof. In one embodiment, the feedstock includes glucose, or a dimer or polymer thereof, or an isomer thereof. In another embodiment, the feedstock includes fructose, or a dimer or polymer thereof, or an isomer thereof. In another variation, the feedstock is a saccharide composition. For example, the saccharide composition may include a single saccharide or a mixture of saccharides such as fructose, glucose, sucrose, lactose and maltose.

Feedstocks suitable for use in the methods and compositions described herein may also include derivatives of the sugars described above. Feedstocks suitable for used in the methods and compositions described herein may be aldoses, ketoses, or any mixtures thereof. In some embodiments, the feedstock includes C6 aldoses, C6 ketoses, or any mixtures thereof. In one embodiment, the feedstock is a C6 aldose. Examples of suitable aldoses include glucose. In another embodiment, the feedstock is a C6 ketose. Examples of suitable ketoses include fructose. In yet another embodiment, the feedstock includes a mixture of C6 aldoses and C6 ketoses. For example, in one variation, the feedstock may include glucose and fructose.

In some embodiments when the feedstock includes sugars, the sugars may be present in open-chain form, cyclic form, or a mixture thereof. For example, glucose as depicted in FIG. 1 is in open-chained form; however, cyclic isomers of glucose may also be used in the method or be present in the reaction mixture. One of skill in the art would recognize that, when the feedstock includes glucose, the open-chain form of glucose used may exist in equilibrium with several cyclic isomers in the reaction.

In other embodiments when the feedstock includes sugars, the sugars can exist as any stereoisomers, or as a mixture of stereoisomers. For example, in certain embodiments, the feedstock may include D-glucose, L-glucose, or a mixture thereof. In other embodiments, the feedstock may include D-fructose, L-fructose, or a mixture thereof.

In one variation, the feedstock includes hexose. One of skill in the art would recognize that hexose is a monosaccharide with six carbon atoms, having the chemical formula $C_6H_{12}O_6$. Hexose may be an aldohexose or a ketohexose, or a mixture thereof. The hexose may be in open-chain form, cyclic form, or a mixture thereof. The hexose may be any stereoisomer, or mixture of stereoisomers. Suitable hexoses may include, for example, glucose, fructose, galactose, mannose, allose, altrose, gulose, idose, talose, psicose, sorbose, and tagatose, or any mixtures thereof.

The feedstock used in the methods and compositions described herein may be obtained from any commercially available sources. For example, one of skill in the art would recognize that cellulose and hemicellulose can be found in biomass (e.g., cellulosic biomass or lignocellulosic biomass). In some embodiments, the feedstock is biomass, which can be any plant or plant-derived material made up of organic compounds relatively high in oxygen, such as carbohydrates, and also contain a wide variety of other organic compounds. The biomass may also contain other materials, such as inorganic salts and clays.

Biomass may be pretreated to help make the sugars in the biomass more accessible, by disrupting the crystalline structures of cellulose and hemicellulose and breaking down the lignin structure (if present). Common pretreatments known in the art involve, for example, mechanical treatment (e.g., shredding, pulverizing, grinding), concentrated acid, dilute acid, $SO_2$, alkali, hydrogen peroxide, wet-oxidation, steam explosion, ammonia fiber explosion (AFEX), supercritical $CO_2$ explosion, liquid hot water, and organic solvent treatments.

Biomass may originate from various sources. For example, biomass may originate from agricultural materials (e.g., corn kernel, corn cob, corn stover, rice hulls, peanut hulls, and spent grains), processing waste (e.g., paper sludge), and recycled cellulosic materials (e.g., cardboard, old corrugated containers (OCC), old newspaper (ONP), and mixed paper). Other examples of suitable biomass may include wheat straw, paper mill effluent, newsprint, municipal solid wastes, wood chips, saw dust, forest thinnings, slash, miscanthus, switchgrass, sorghum, bagasse, manure, wastewater biosolids, green waste, and food/feed processing residues.

A combination of any of the feedstocks described herein may also be used. For example, in one variation, the feedstock may include glucose, corn kernel and wood chips. In another variation, the feedstock may include wood chips and cardboard. In yet another variation, the feedstock may include bagasse and cardboard.

Acid

Types of Acid

The acids used in the methods and compositions described herein are halogen-containing acids. Such acids have a formula HX, wherein X is halo. Any suitable acids that can cause dehydration and ring cyclization to produce 5-(halomethyl)furfural may be used. In some embodiments, the acids is a halogen-containing mineral acid or a halogen-containing organic acid. A mixture of acids may also be used.

In certain embodiments, the acid may be a chloride acid, or an acid having a chloride ion. In one embodiment, the acid is hydrochloric acid. When a chloride acid, an acid having a chloride ion or hydrochloric acid is used, the 5-(halomethyl)furfural is 5-(chloromethyl)furfural (CMF).

In certain embodiments, the acid may be a bromide acid, or an acid having a bromide ion. In one embodiment, the acid is hydrobromic acid. When a bromide acid, an acid having a bromide ion or hydrobromic acid is used, the 5-(halomethyl)furfural is 5-(bromomethyl)furfural (BMF).

The acid used in the methods and compositions described herein may be aqueous and/or gaseous. In some embodiments, the acid is an aqueous acid. "Aqueous acid" refers to an acid dissolved, or at least partially dissolved, in water. In certain embodiments, the aqueous acid is hydrochloric acid, hydrobromic acid, nitric acid, phosphoric acid, sulfuric acid, and fluoroboric acid. One of skill in the art would recognize that when nitric acid, phosphoric acid, sulfuric acid, or fluoroboric acid is used, such acid may be employed as one of the reagents to produce an acid of formula HX, wherein X is halo, in situ. In one variation, the acid of formula HX may be provided by reacting an aqueous acid (e.g., nitric acid, phosphoric acid, sulfuric acid, or fluoroboric acid) with a halide salt.

Thus, the acid used herein may be obtained from any commercially available source, or be produced in situ from providing suitable reagents to the reaction mixture. For example, hydrochloric acid may be produced in situ in the reaction mixture by providing sulfuric acid and sodium chloride to the reaction mixture. Thus, in some embodiments, provided is method of producing 5-(chloromethyl)furfural by: a) combining a feedstock, sulfuric acid, sodium chloride, and lithium chloride in a reaction vessel to form a reaction mixture, wherein the sulfuric acid and sodium chloride forms hydrochloric acid in situ; and b) converting at least a portion of the feedstock in the reaction mixture to produce 5-(chloromethyl)furfural.

In other embodiments, the acid fed into the reactor or the reaction mixture is a gaseous acid. For example, at least a portion of such gaseous acid may be dissolved, or partially dissolved, in the reaction mixture to produce an aqueous acid.

Acid Concentration

The concentration of the acid used in the methods and compositions described herein is typically less than 12 M. One of skill in the art would recognize that concentrated hydrochloric acid is 12 M. In some embodiments, the acid used in the methods and compositions described herein has a concentration less than 12 M, less than or equal to 11.5 M, less than or equal to 11 M, less than or equal to 10.5 M, less than or equal to 10 M, less than or equal to 9.5 M, less than or equal to 9 M, less than or equal to 8.5 M, less than or equal to 8 M, less than or equal to 7.5 M, less than or equal to 7 M, less than or equal to 6.5 M, less than or equal to 6 M, less than or equal to 5.5 M, less than or equal to 5 M, less than or equal to 4.5 M, less than or equal to 4 M, less than or equal to 3.5 M, less than or equal to 3 M, less than or equal to 2.5 M, less than or equal to 2 M, less than or equal to 1.5 M, or less than or equal to 1 M; or between 0.25 M and 10 M, between 0.25 M and 9 M, between 0.25 M and 8 M, between 0.25 M and 7 M, between 0.25 M and 6 M, between 0.25 M and 5 M, between 0.5 M and 10 M, between 0.5 M and 9 M, between 0.5 M and 8 M, between 0.5 M and 7 M, between 0.5 M and 6 M, between 0.5 M and 5 M, between 1 M and 10 M, between 1 M and 9 M, between 1 M and 8 M, between 1 M and 7 M, between 1 M and 6 M, between 1 M and 5 M, between 1 M and 4 M, or between 2 M and 4 M.

The concentration of the acid used herein may also vary depending on various factors, including the type of feedstock used. In some embodiments when the feedstock is or includes an aldose, the acid has a concentration less than 12 M, less than or equal to 11 M, less than or equal to 10 M, less than or equal to 9 M, less than or equal to 8 M, less than or equal to 7 M, less than or equal to 6 M, less than or equal to 5 M, less than or equal to 4 M, less than or equal to 3 M, or less than or equal to 2 M; or between 0.25 M and 11.5 M, between 0.25 M and 10 M, between 0.5 M and 8 M, between 0.5 and 6 M, or between 0.5 and 5 M.

In certain embodiments when the feedstock is or includes glucose, the acid has a concentration less than 12 M, less than or equal to 11 M, less than or equal to 10 M, less than or equal to 9 M, less than or equal to 8 M, less than or equal to 7 M, less than or equal to 6 M, less than or equal to 5 M, less than or equal to 4 M, less than or equal to 3 M, or less than or equal to 2 M; or between 0.25 M and 11.5 M, between 0.25 M and 10 M, between 0.5 M and 8 M, between 0.5 and 6 M, or between 0.5 and 5 M.

In one embodiment when the feedstock is or includes glucose and hydrochloric acid is the acid used, the hydrochloric acid has a concentration less than 12 M, less than or equal to 11 M, less than or equal to 10 M, less than or equal to 9 M, less than or equal to 8 M, less than or equal to 7 M, less than or equal to 6 M, less than or equal to 5 M, less than or equal to 4 M, less than or equal to 3 M, or less than or equal to 2 M; or between 0.25 M and 11.5 M, between 0.25 M and 10 M, between 0.5 M and 8 M, between 0.5 and 6 M, or between 0.5 and 5 M.

In other embodiments when the feedstock is or include ketose, the acid has a concentration less than or equal to 6 M, less than or equal to 5 M, less than or equal to 4 M, less than or equal to 3 M, less than or equal to 2 M, or less than or equal to 1 M; or between 0.25 M and 6 M, between 0.25 M and 5 M, between 0.25 M and 4 M, between 0.25 M and 3 M, between 0.25 M and 2 M, between 0.5 M and 6 M, between 0.5 M and 5 M, between 0.5 M and 4 M, between 0.5 M and 3 M, between 0.5 M and 2 M, between 1 M and 6 M, between 1 M and 5 M, between 1 M and 4 M, between 1 M and 3 M, or between 1 M and 2M.

In other embodiments when the feedstock is or include fructose, the acid has a concentration less than or equal to 6 M, less than or equal to 5 M, less than or equal to 4 M, less than or equal to 3 M, less than or equal to 2 M, or less than or equal to 1 M; or between 0.25 M and 6 M, between 0.25 M and 5 M, between 0.25 M and 4 M, between 0.25 M and 3 M, between 0.25 M and 2 M, between 0.5 M and 6 M, between 0.5 M and 5 M, between 0.5 M and 4 M, between 0.5 M and 3 M, between 0.5 M and 2 M, between 1 M and 6 M, between 1 M and 5 M, between 1 M and 4 M, between 1 M and 3 M, or between 1 M and 2M.

In other embodiments when the feedstock is or include fructose and hydrochloric acid is the acid used, the hydrochloric acid has a concentration less than or equal to 6 M, less than or equal to 5 M, less than or equal to 4 M, less than or equal to 3 M, less than or equal to 2 M, or less than or equal to 1 M; or between 0.25 M and 6 M, between 0.25 M and 5 M, between 0.25 M and 4 M, between 0.25 M and 3 M, between 0.25 M and 2 M, between 0.5 M and 6 M, between 0.5 M and 5 M, between 0.5 M and 4 M, between 0.5 M and 3 M, between 0.5 M and 2 M, between 1 M and 6 M, between 1 M and 5 M, between 1 M and 4 M, between 1 M and 3 M, or between 1 M and 2M.

$H^+$ Concentration

The concentration of acid(s) used in the methods and compositions described herein affects the $H^+$ concentration in the reaction mixture. In some embodiments, the $[H^+]$ in the reaction mixture is less than 12 M, less than or equal to 11.5 M, less than or equal to 11 M, less than or equal to 10.5 M, less than or equal to 10 M, less than or equal to 9.5 M, less than or equal to 9 M, less than or equal to 8.5 M, less than or equal to 8 M, less than or equal to 7.5 M, less than or equal to 7 M, less than or equal to 6.5 M, less than or equal to 6 M, less than or equal to 5.5 M, less than or equal to 5 M, less than or equal to 4.5 M, less than or equal to 4 M, less than or equal to 3.5 M, less than or equal to 3 M, less than or equal to 2.5 M, less than or equal to 2 M, less than or equal to 1.5 M, or less than or equal to 1 M; or between 0.25 M and 10 M, between 0.25 M and 9 M, between 0.25 M and 8 M, between 0.25 M and 7 M, between 0.25 M and 6 M, between 0.25 M and 5 M, between 0.5 M and 10 M, between 0.5 M and 9 M, between 0.5 M and 8 M, between 0.5 M and 7 M, between 0.5 M and 6 M, between 0.5 M and 5 M, between 1 M and 10 M, between 1 M and 9 M, between 1 M and 8 M, between 1 M and 7 M, between 1 M and 6 M, between 1 M and 5 M, between 1 M and 4 M, or between 2 M and 4 M.

In certain embodiments, the $[H^+]$ in the reaction mixture is less than 0.6 M, less than 0.55 M, less than 0.5 M, less than 0.45 M, less than 0.4 M, less than 0.35 M, less than 0.3 M, less than 0.25 M, less than 0.2 M, less than 0.15 M, less than 0.1 M, less than 0.05M, or less than 0.01 M.

It should be understood that the $[H^+]$ of the reaction mixture may depend on the concentration of acid or acids used in the methods and compositions described herein.

It should also generally be understood that $H^+$ is present in sufficient quantities in the methods described herein to allow the reaction to proceed. Thus, in some embodiments, the $[H^+]$ is greater than 0 M. For example, in some variations, the $[H^+]$ is greater than or equal to 0.0001 M, 0.001 M, or 0.1 M.

In other embodiments, the $[H^+]$ in the reaction mixture is between the feedstock concentration and 5 M. The feedstock concentration refers to the molar concentration of C6 monosaccharides, or monomeric units have six carbon atoms.

The acid concentrations as described herein may refer to the initial concentrations, fed concentrations, or steady-state concentrations. Initial concentration refers to the concentration of the reaction mixture at the point in time when the reaction begins. Fed concentration refers to the concentration when the reactants are combined before being fed into the reactor. Steady-state concentration refers to concentration at steady state of the reaction.

In some variations, the acid is added continuously to the reaction mixture at a rate to maintain a non-zero $[H^+]$. It should be understood that the acid is consumed in a stoichiometric amount. For example, 1 mole of CMF requires 1 mole of $H^+$ and 1 mole of glucose.

Salt

Types of Salt

The salts used in the methods and compositions described herein may be inorganic salts and/or organic salts. An "inorganic salt" refers to a complex of a positively charged species and a negatively charged species, where neither species includes the element carbon. An "organic salt" refers to a complex of a positively charged species and a negatively charged species, where at least one species includes the element carbon.

The selection of the salt used may vary depending on the reaction conditions, as well as the acid and solvent used. In some embodiments, the salt is an inorganic salt. In certain embodiments, the salt is a halogen-containing acid.

In some embodiments, the salt is $A^{r+}(X^-)_r$, wherein:

$A^{r+}$ is a Group I or Group II cation; and $X^-$ is an halo anion.

It should be understood that variable "r" refers to the ionic charge. In certain variations, the salt has a monovalent or divalent cation. In other words, in certain variations, r may be 1 or 2.

Examples of salts that may be used in certain embodiments include lithium salts, sodium salts, potassium salts, rubidium salts, cesium salts, magnesium salts, and calcium salts. In some embodiments, the salt is a lithium salt. In other embodiments, the salt is a calcium salt. In some variations, $A^{r+}$ is $Li^+$, $Na^+$, $K^+$, $Rb^+$, $Cs^+$, $Mg^{2+}$, $Ca^{2+}$, or $Sr^{2+}$. In certain variations, $A^{r+}$ is $Li^+$, $Mg^{2+}$, or $Ca^{2+}$. In some variations, $X^-$ is $Cl^-$ or $Br^-$. In certain variations, the salt is LiX, NaX, KX, RbX, CsX, $MgX_2$, $CaX_2$, or $SrX_2$. In one variation, X is Cl or Br. In some variations, the salt is LiCl, NaCl, KCl, RbCl, CsCl, $MgCl_2$, $CaCl_2$, $SrCl_2$, LiBr, NaBr, KBr, RbBr, CsBr, $MgBr_2$, $CaBr_2$, or $SrBr_2$. In certain variations, the salt is selected from LiCl, MgCl$_2$, CaCl$_2$, NaCl, KCl, CsCl, LiBr, MgBr$_2$, NaBr, KBr, and CsBr. In one variation, the salt is LiCl. In another variation, the salt is CaCl$_2$.

A combination of any of the salts described herein may also be used. For example, in some variations, LiCl and CaCl$_2$ may be used together as the salt. In other variations, additional salts may also be used. Such additional salts may be selected from, for example, zinc salts, silicate salts, carbonate salts, sulfate salts, sulfide salts, phosphate salts, perchlorate salts, and triflate salts. In certain embodiments, the additional salt is selected from ZnCl$_2$, lithium triflate (LiOTf), and sodium triflate (NaOTf), or any combination thereof. In one variation, a combination of LiCl and LiOTf is used as the salt.

Salt Concentration

The concentration of the salt used in the methods and compositions described herein may vary. In some embodiments, the concentration of the salt(s) is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M.

For example, in some embodiments when LiCl is the salt used, the concentration of LiCl is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the LiCl is present from about 0.1% to 50% (w/w) of the aqueous phase.

In other embodiments when CaCl$_2$ is the salt used, the concentration of CaCl$_2$ is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the CaCl$_2$ is present from about 0.1% to 50% (w/w) of the aqueous phase.

In other embodiments when MgCl$_2$ is the salt used, the concentration of MgCl$_2$ is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the MgCl$_2$ is present from about 0.1% to 50% (w/w) of the aqueous phase.

In some embodiments when the salt used is LiCl, CaCl$_2$, MgCl$_2$, or a mixture thereof, the salt concentration is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the salt or mixture of salts is present from about 0.1% to 50% (w/w) of the aqueous phase.

In some embodiments when LiBr is the salt used, the concentration of LiBr is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the LiBr is present from about 0.1% to 50% (w/w) of the aqueous phase.

In other embodiments when CaBr$_2$ is the salt used, the concentration of CaBr$_2$ is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the CaBr$_2$ is present from about 0.1% to 50% (w/w) of the aqueous phase.

In other embodiments when MgBr$_2$ is the salt used, the concentration of MgBr$_2$ is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the MgBr$_2$ is present from about 0.1% to 50% (w/w) of the aqueous phase.

In some embodiments when the salt used is LiBr, CaBr$_2$, MgBr$_2$, or a mixture thereof, the salt concentration is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M. In other embodiments, the salt or mixture of salts is present from about 0.1% to 50% (w/w) of the aqueous phase.

X$^-$ Concentration

The concentration of salt(s) and acid(s) used may affects the concentration of the positively charged ions and the negatively charged ions present in the reaction mixture. As discussed above, the salt may be depicted by the formula $A^{r+}(X^-)_r$, where $A^{r+}$ is a cation having ionic charge "r", and X$^-$ is a halo anion. The cation concentration present in the reaction mixture may be defined by the following equation:

$$\text{cation concentration} = \frac{|[X^-] - [H^+]|}{\text{valence of cation}},$$

where X is halo.

It should generally be understood that [H$^+$] refers to the H$^+$ concentration; and [X$^-$] refers to the X$^-$ concentration.

In some embodiments, the [X$^-$] in the reaction mixture is greater than 2 M, greater than 5 M, greater than 6 M, greater than 7 M, greater than 8 M, greater than 9 M, greater than 10 M; or between 2 M to 25 M, between 5 M and 20 M, between 5 M and 15 M, between 5 M and 12 M, between 6 M and 12 M, between 5.5 M and 10 M, between 7 M and 10 M, between 7.5 M and 9 M, or between 6 M and 12 M; or about 10 M, about 11 M, about 12 M, about 13 M, about 14 M, or about 15 M.

For example, when the acid used is hydrochloric acid (HCl) and the salt used is lithium chloride (LiCl), calcium chloride (CaCl$_2$), or a mixture thereof, X$^-$ is Cl$^-$. Thus, in one variation, the [Cl$^-$] in the reaction mixture is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M.

In another example, when the acid used is hydrobromic acid (HBr) and the salt used is lithium bromide (LiBr), calcium bromide (CaBr$_2$), X$^-$ is Br$^-$. Thus, in one variation, the [Br$^-$] in the reaction mixture is greater than 5 M, greater than 6 M, greater than 7 M, greater than 8 M, greater than 9 M, or greater than 10 M; or between 5 M and 20 M, between 5 M and 15 M, between 5.5 M and 10 M, between 7 M and 10 M, or between 7.5 M and 9 M; or about 10 M, about 11 M, about 12 M, about 13 M, about 14 M, or about 15 M.

It is understood that any description of acid for use in the methods and compositions described herein may be combined with any descriptions of the salts the same as if each and every combination were individually listed. For example, in some embodiments, the acid is hydrochloric acid, and the salt is lithium chloride, calcium chloride, or a mixture thereof. In one variation, the acid is hydrochloric acid, and the salt is lithium chloride. In another variation, the acid is hydrochloric acid, and the salt is calcium chloride. In yet another variation, the acid is hydrochloric acid, and the salt is a mixture of lithium chloride and calcium chloride. In other variations, the acid is hydrobromic acid, and the salt is lithium bromide and calcium bromide.

It is further understood that any description of acid concentration or [H$^+$] in the methods and compositions described herein may be combined with any description of the salt concentration or [X$^-$] the same as if each and every combination were individually listed. In some embodiments, the [H$^+$] in the reaction mixture is greater than 0 M and less than 8M; and the [X$^-$] in the reaction mixture is at least 5 M. In other embodiments, the [H$^+$] in the reaction mixture is greater than 0 M and less than 8M; and the [X–] in the reaction mixture is at least 10 M.

For example, in other embodiments where the acid is hydrochloric acid and the salt is lithium chloride, the hydrochloric acid concentration is between 0.5 M and 9 M, and the lithium chloride concentration is between 5M and 20 M. In one variation, the hydrochloric acid concentration is between 0.5 M and 6 M, and the lithium chloride concentration is about 12 M. In other embodiments where the acid is hydrochloric acid, and the salt is lithium chloride, calcium chloride, or a mixture thereof, the reaction mixture has a [H$^+$] between 0.5 M and 9 M, and a [Cl$^-$] between 5M and 20 M. In one variation, the reaction mixture has a [H$^+$] between 0.5 M and 6 M, and the reaction mixture has a [Cl$^-$] of about 12 M.

The salt used herein may be obtained from any commercially available source, or be produced in situ from providing suitable reagents to the reaction mixture. For example, certain reagents in the presence of hydrochloric acid may undergo ion exchange to produce the chloride salt used in the methods described herein.

The concentrations described herein for the salt or [X$^-$] (e.g., [Cl$^-$]) may refer to either initial concentrations, fed concentrations or steady-state concentrations.

Solvent System

A solvent, or a combination or mixture of solvents, may also be optionally added to the reaction mixture. The solvents used in the methods and compositions described herein may be obtained from any source, including any commercially available sources. In some embodiments, the methods described herein are performed neat (i.e., without the use of any solvents). In other embodiments, the method includes combining a feedstock, an aqueous acid, a salt, and a solvent system in a reaction vessel to form a reaction mixture.

Any suitable solvent systems that can form a liquid/liquid biphase in the reaction mixture may be used, such that one phase is predominantly an organic phase and a separate phase is predominantly an aqueous phase. The 5-(halomethyl)furfural typically partitions between the organic phase and the aqueous phase such that the concentration of 5-(halomethyl)furfural in the organic phase is at least 20%, at least 25%, at least 30%, at least 35%, at least 40%, at least 45%, at least 50%, at least 55%, or at least 60% of the 5-(halomethyl)furfural concentration in the aqueous phase.

The solvent systems used in the methods and compositions described herein may also be selected based on their dipole moment. One of skill in the art would understand that the dipole moment is a measure of polarity of a solvent. The dipole moment of a liquid can be measured with a dipole meter. In some embodiments, the solvent system used herein has a dipole moment less than 20.1 D, less than or equal to 20 D, less than or equal to 18 D, or less than or equal to 15 D.

The solvent system used in the methods and compositions described herein may also be selected based on their boiling points. In some embodiments, the solvent system has a boiling point of at least 110° C., at least 150° C., or at least 240° C.

The solvent system used in the methods and compositions described herein may also be selected based on the partition coefficient of the 5-(halomethyl)furfural in the reaction mixture. As used herein, "partition coefficient" refers to the ratio of molar concentration of 5-(halomethyl)furfural in the organic phase to 5-(halomethyl)furfural in the aqueous phase in the reaction mixture. In some embodiments, the partition coefficient of the 5-(halomethyl)furfural in the reaction mixture is at least 0.2, at least 1, at least 10, or at least 100; or between 0.2 and 200, between 0.2 and 150, between 1 and 100.

The solvent system may include a solvent or a mixture of solvents. For example, in some embodiments, the solvent system includes one or more alkyl phenyl solvents, one or more alkyl solvents (e.g., heavy alkyl solvents), one or more ester solvents, one or more aromatic solvents, one or more silicone oils, or any combinations or mixtures thereof. In other embodiments, the solvent system includes one or more hydrocarbons, one or more halogenated hydrocarbons, one or more ethers, one or more halogenated ethers, one or more cyclic ethers, one or more amides, one or more silicone oils, or any combinations or mixtures thereof.

In some embodiments, the solvent system includes para-xylene, mesitylene, naphthalene, anthracene, toluene, dodecylbenzene, pentylbenzene, hexylbenzene, and other alkyl benzenes (e.g., Wibaryl® A, Wibaryl® B, Wibaryl® AB, Wibaryl® F, Wibaryl® R, Cepsa Petrepar® 550-Q, Cepsa Petrepar® 900-Q, Santovac® 5, Santovac® 7, Marlican®, Synnaph AB 3, Synnaph AB4), sulfolane, hexadecane, heptadecane, octadecane, icosane, heneicosane, docosane, tricosane, tetracosane, or any combinations or mixtures thereof.

It should be understood that the solvent may fall into one or more of the classes listed herein. For example, the solvent system may include para-xylene, which is an alkyl phenyl solvent and an aromatic solvent.

Alkyl Phenyl Solvents

As used herein, "an alkyl phenyl solvent" refers to a class of solvents that may have one or more alkyl chains and one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)pentane and pentylbenzene refer to the same solvent.

In some embodiments, the solvent system includes an alkylbenzene. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include pentylbenzene, hexylbenzene and dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl rings.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains.

In some embodiments, the solvent system includes phenylalkane. Examples may include (monophenyl)alkanes, (diphenyl)alkanes, and (polyphenyl)alkanes. In certain embodiments, the phenylalkane has one phenyl ring attached to one alkyl chain. The phenyl ring may be attached to any carbon along the alkyl chain. For example, the phenyl alkyl having one alkyl chain may be (1-phenyl)pentane, (2-phenyl)pentane, (1-phenyl)hexane, (2-phenyl)hexane, (3-phenyl)hexane, (1-phenyl)dodecane, and (2-phenyl)dodecane.

In other embodiments, the phenylalkane has two or more phenyl rings attached to one alkyl chain.

In one embodiment, the solvent system includes Wibaryl® A, Wibaryl® B, Wibaryl® AB, Wibaryl® F, Wibaryl® R, Cepsa Petrepar® 550-Q, or any combinations or mixtures thereof. In another embodiment, the solvent system includes para-xylene, toluene, or any combinations or mixtures thereof.

In certain embodiments, the alkyl chain of a solvent may be 1 to 20 carbon atoms (e.g., $C_{1-20}$ alkyl). In one embodiment, the alkyl chain may be 4 to 15 carbons (e.g., $C_{4-15}$ alkyl), or 10 to 13 carbons (e.g., $C_{10-13}$ alkyl). The alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the solvent system includes a linear alkylbenzene ("LAB"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the solvent system includes a hard type dodecylbenzene.

In some embodiments, the solvent system includes any of the alkyl phenyl solvents described above, in which the phenyl ring is substituted with one or more halogen atoms. In certain embodiments, the solvent system includes an alkyl(halobenzene). For example, the alkyl(halobenzene) may include alkyl(chlorobenzene). In one embodiment, the halo substituent for the phenyl ring may be, for example, chloro, bromo, or any combination thereof.

In other embodiments, the solvent system includes naphthalene, naphthenic oil, alkylated naphthalene, diphenyl, polychlorinated biphenyls, polycyclic aromatic hydrocarbons, or halogenated hydrocarbons.

Aliphatic Solvents

In one embodiment, the solvent system includes an aliphatic solvent. The aliphatic solvent may be linear, branched, or cyclic. The aliphatic solvent may also be saturated (e.g., alkane) or unsaturated (e.g., alkene or alkyne). In some embodiments, the solvent system includes a C1-C20 aliphatic solvent, a C1-C10, aliphatic solvent, or a C1-C6 aliphatic solvent. In certain embodiments, the solvent system includes a C4-C30 aliphatic solvent, a C6-C30 aliphatic solvent, a C6-C24 aliphatic solvent, or a C6-C20 aliphatic solvent. In certain embodiments, the solvent system includes C8+ alkyl solvent, or a C8-C50 alkyl solvent, a C8-C40 alkyl solvent, a C8-C30 alkyl solvent, a C8-C20 alkyl solvent, or a C8-C16 alkyl solvent. Suitable aliphatic solvents may include, for example, butane, pentane, cyclopentane, hexane, cyclohexane, heptane, cycloheptane, octane, cyclooctane, nonane, decane, undecane, dodecane, hexadecane, or any combinations or mixtures thereof. In certain embodiments, the aliphatic solvent is linear.

The aliphatic solvent may be obtained from petroleum refining aliphatic fractions, including any isomers of the aliphatic solvents, and any mixtures thereof. For example, alkane solvents may be obtained from petroleum refining alkane fractions, including any isomers of the alkane solvents, and any mixtures thereof. In certain embodiments, the solvent system includes petroleum refining alkane fractions.

Aromatic Solvents

In another embodiment, the solvent system includes an aromatic solvent. In some embodiments, the solvent system includes a C6-C20 aromatic solvent, a C6-C12 aromatic solvent, or a C13-C20 aromatic solvent. The aromatic solvent may be optionally substituted. Suitable aromatic solvents may include, for example, para-xylene, mesitylene, naphthalene, anthracene, toluene, anisole, nitrobenzene, bromobenzene, chlorobenzene (including, for example, dichlorobenzene), dimethylfuran (including, for example, 2,5-dimethylfuran), and methylpyrrole (including, for example, N-methylpyrrole).

Ether Solvents

In other embodiments, the solvent system includes an ether solvent, which refers to a solvent having at least one ether group. For example, the solvent system includes a C2-C20 ether, or a C2-C10 ether. The ether solvent can be non-cyclic or cyclic. For example, the ether solvent may be alkyl ether (e.g., diethyl ether, glycol dimethyl ether (glyme), diethylene glycol dimethyl ether (diglyme), or triethylene glycol dimethyl ether (triglyme)). In another example, the ether solvent may be cyclic, such as dioxane (e.g., 1,4-dioxane), dioxin, tetrahydrofuran, or a cycloalkyl alkyl ether (e.g., cyclopentyl methyl ether).

The solvent system may include an acetal such as dioxolane (e.g., 1,3-dioxolane).

The solvent system may also include a polyether with two or more oxygen atoms. In some embodiments, the ether solvent has a formula as follows:

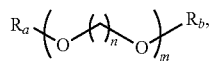

where each $R_a$ and $R_b$ are independently aliphatic moieties, and n and m are integers equal to greater than 1. In some embodiments, each $R_a$ and $R_b$ are independently alkyl. In certain embodiments, each $R_a$ and $R_b$ are independently C1-C10 alkyl, or C1-C6 alkyl. $R_a$ and $R_b$ may be the same or different. In other embodiments, each n and m are independently 1 to 10, or 1 to 6, where n and m may be the same or different.

The formula above includes proglymes (such as dipropylene glycol dimethylether), or glymes (such as glycol diethers based on ethylene oxide). In one embodiment, the solvent system includes glyme, diglyme, triglyme, or tetraglyme.

It should also be understood that a solvent having an ether group may also have one or more other functional groups. It should be understood, however, that the solvent may have an ether functional group in combination with one or more additional functional groups, such as alcohols. For example, the solvent system includes alkylene glycols (e.g., ethylene glycol, diethylene glycol, triethylene glycol, polyethylene glycol), phenyl ethers (e.g., diphenyl ether, polyphenyl ethers), or alkylphenylethers (e.g., alkyldiphenyl ether).

In certain embodiments, the solvent system includes a polyphenyl ether that includes at least one phenoxy or at least one thiophenoxy moiety as the repeating group in ether linkages. For example, in one embodiment, the solvent system includes Santovac.

Ester Solvents

In yet other embodiments, the solvent system includes an ester solvent, which refers to a solvent having at least one ester group. For example, the solvent system includes a C2-C20 ester, or a C2-C10 ester. The ester solvent can be non-cyclic (linear or branched) or cyclic. For example, non-cyclic ester solvents may include alkyl acetate (e.g., methyl acetate, ethyl acetate, propyl acetate, butyl acetate), triacetin, and dibutylphthalate. An example of cyclic ester is, for example, propylene carbonate. It should be understood, however, that a solvent having an ester group may also have one or more other functional groups. The ester solvent may also include alkyl lactate (e.g., methyl lactate, ethyl lactate, propyl lactate, butyl lactate), which has both an ester group as well as a hydroxyl group.

Halogenated Solvents

In yet other embodiments, the solvent system includes haloginated solvents. For example, the solvent can be a chlorinated solvent. Suitable chlorinated solvents may include, for example, carbon tetrachloride, chloroform, methylene chloride, bromobenzene and dichlorobenzene.

Other Solvents

In some variations, the solvent includes water.

Solvent Combinations or Mixtures

A combination or mixture of solvents may also be used in the methods and compositions described herein. In some embodiments, an ether solvent may be combined with one or more other types of solvents listed above.

Amount of Solvent(s) Used

The solvents used in the methods and compositions described herein may vary depending on the type and amount of feedstock used. For example, in some embodiments, the mass to volume ratio of feedstock to solvent system is between 1 g and 30 g feedstock per 100 mL solvent system.

It is further understood that any description of the solvents used in the methods and compositions described herein may be combined with any description of the acids and salts the same as if each and every combination were individually listed. For example, in some embodiments, the acid is hydrochloric acid, the salt is lithium chloride or calcium chloride, or a combination thereof, and the solvent is an alkyl phenyl solvent. In certain variations, the acid is hydrochloric acid, the salt is lithium chloride, the reaction mixture has a [$H^+$] between 0.5 M and 9 M and a [$Cl^-$] between 5M and 20 M, and the solvent is para-xylene.

Reaction Conditions

As used herein, "reaction temperature" and "reaction pressure" refer to the temperature and pressure, respectively, at which the reaction takes place to convert at least a portion of the six-carbon sugars in the feedstock into 5-(halomethyl) furfural.

In some embodiments of the methods described herein, the reaction temperature is at least 15° C., at least 25° C., at least 30° C., at least 40° C., at least 50° C., at least 60° C., at least 70° C., at least 80° C., at least 90° C., at least 100° C., at least 110° C., at least 115° C., at least 120° C., at least 125° C., at least 130° C., at least 135° C., at least 140° C., at least 145° C., at least 150° C., at least 175° C., at least 200° C., at least 250° C., or at least 300° C. In other embodiments, the reaction temperature is between 110° C. and 300° C., between 110° C. to 250° C., between 150° C. and 300° C., or between 110° C. and 250° C.

The reaction temperature selected may vary depending on the various factors, including, for example, the type of feedstock and the concentration of acid used. In certain variation, when the feedstock is or includes ketose sugars, the reaction may be performed at lower temperatures compared to when the feedstock is or includes aldose sugars. For example, in one variation, when the feedstock includes fructose, the reaction may be performed at a temperature of at least 15° C. In another variation, when the feedstock include glucose, the reaction is performed at a temperature of at least 115° C., and the reaction proceeds at lower [$H^+$], e.g., less than 1 M. 5-(Halomethyl)furfural was unexpectedly observed to be produced with improved selectivity under such conditions (e.g., lower [$H^+$]).

In some embodiments of the methods described herein, the reaction pressure is between 0.1 atm and 10 atm. In other embodiments, the reaction pressure is atmospheric pressure.

It should be understood that temperature may be expressed as degrees Celsius (° C.) or Kelvin (K). One of ordinary skill in the art would be able to convert the temperature described herein from one unit to another. Pressure may also be expressed as gauge pressure (barg), which refers to the pressure in bars above ambient or atmospheric pressure. Pressure may also be expressed as bar, atmosphere (atm), pascal (Pa) or pound-force per square inch (psi). One of ordinary skill in the art would be able to convert the pressure described herein from one unit to another.

Figure 3:
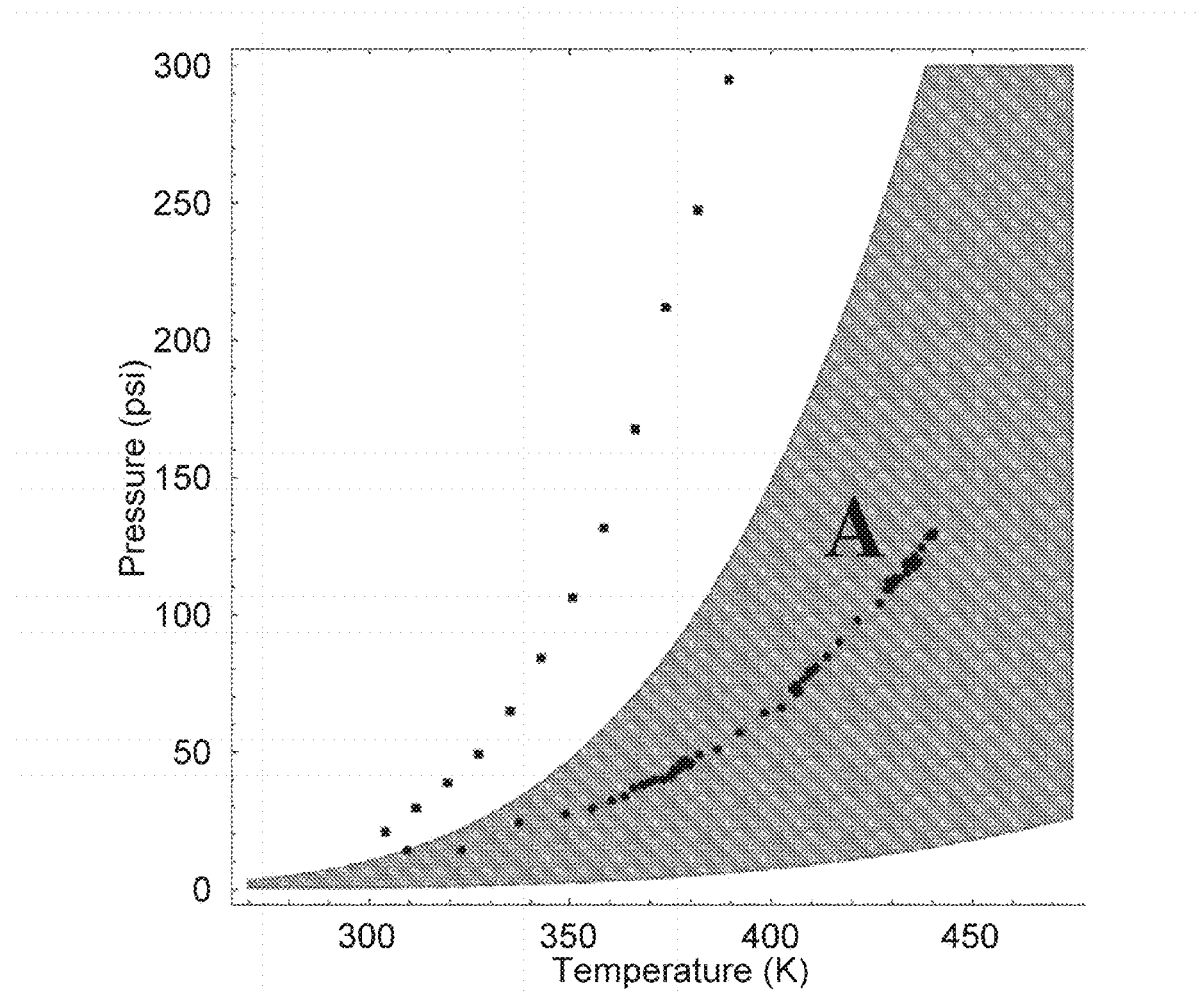
FIG. 3 is a graph depicting exemplary reaction temperatures and reaction temperatures in region A for the methods described herein.

The reaction temperature and reaction pressure of the methods described herein may also be expressed as a relationship. For example, in one variation, at least a portion of the feedstock is converted into 5-(chloromethyl)furfural at a reaction temperature T expressed in Kelvin and a reaction pressure P expressed in psi, wherein $10<\text{Ln}[P/(1\,\text{psi})]+2702/(T/(1\,\text{K}))<13$. In another variation, at least a portion of the feedstock is converted into 5-(chloromethyl) furfural at a reaction temperature and a reaction pressure in region A of FIG. 3.

The residence time will also vary with the reaction conditions and desired yield. Residence time refers to the average amount of time it takes to produce 5-(halomethyl) furfural from the feedstock in the reaction mixture. The methods described herein can produce 5-(halomethyl)furfural with residence times less than 360 minutes, less than 240 minutes, less than 120 minutes, less than 60 minutes, less than 30 minutes, less than 20 minutes, less than 10 minutes, less than 5 minutes, or less than 2 minutes. In one variation, at least 50%, at least 60%, at least 70%, at least 75%, at least 80%, at least 85%, at least 90%, at least 95%, or at least 99% of the feedstock is converted into 5-(chloromethyl)furfural in less than 12 hours. In another variation, at least 50% of the feedstock is converted into 5-(chloromethyl)furfural in less than 12 hours, less than 11 hours, less than 10 hours, less than 9 hours, less than 8 hours, less than 7 hours, less than 6 hours, less than 5 hours, less than 4 hours, less than 3 hours, less than 2 hours, less than 60 minutes, less than 45 minutes, less than 30 minutes, less than 20 minutes or less than 10 minutes.

In certain embodiments, at least 70%, at least 75%, at least 80%, at least 85%, at least 90%, at least 95%, or at least 99% of the feedstock is converted to 5-(halomethyl)furfural at a reaction temperature of at least 140° C. in 20 minutes or less. In certain embodiments, at least 50%, at least 55%, at least 60%, at least 65%, at least 70%, at least 75%, at least 80%, at least 85%, at least 90%, at least 95%, or at least 99% of the feedstock is converted to 5-(halomethyl)furfural at a reaction temperature of at least 170° C. in 10 minutes or less.

Isolation of 5-(Halomethyl)furfural

The converting of at least a portion of the feedstock in the reaction mixture produces a product mixture that has one or more aqueous phases and one or more organic phases. The aqueous phase(s) and the organic phase(s) each independently has at least a portion of 5-(halomethyl)furfural.

At the completion of the reaction, at least a portion of the 5-(halomethyl)furfural produced is soluble in the organic phase of the biphasic reaction mixture. At the reaction temperature, the 5-(halomethyl)furfural and the organic solvent (if used) form one organic phase. The organic phase is separated from the aqueous phase to isolate the product-containing phase, and then cooled to a temperature at which at least a portion of the 5-(halomethyl)furfural and the organic solvent forms multiple phases. The 5-(halomethyl) furfural can then be isolated from the organic phase. Thus, in some embodiments, the methods described herein further includes isolating the 5-(halomethyl)furfural from the reaction mixture.

The methods described herein may also include purifying the isolated 5-(halomethyl)furfural. Any suitable methods known in the art may be employed to purify the isolated 5-(halomethyl)furfural, including for example column chromatography or recrystallization.

Reactors and Vessels

The methods described herein may be carried out batchwise or continuously. The production of 5-(halomethyl) furfural from the feedstock may be performed in any suitable reactors, including open or closed reactors, that can contain the chemical reactions described herein. Suitable reactors may include, for example, a fed-batch stirred reactor, a batch stirred reactor, a continuous flow stirred reactor, a continuous plug-flow column reactor, an attrition reactor, a fluidized bed reactor. The reactor may include a continuous mixer, such as a screw mixer.

Additionally, the reactor may allow for addition and removal of certain components in the reaction mixture. For example, the reactor can have one or more outlets to add additional solvent or acid, or to remove the organic or aqueous phase from the reaction mixture. In some embodiments, the reactor may have one or more outlets that connecting the reactor to an isolation vessel, where the organic phase can be transferred from the reactor to the isolation vessel.

The reactors and vessels used herein may be generally made up of materials that are capable of withstanding the physical and chemical forces exerted during the methods described herein. In some embodiments, such materials used are capable of tolerating high concentrations of strong liquid acids. For example, the reactors and vessels may be made up of glass, metal or pyrex.

5-(Halomethyl)furfural and Downstream Products

The 5-(halomethyl)furfural produced according to the methods described herein may be used in other chemical reactions, or further converted into other furanic derivatives for biofuels, diesel additives, or plastics.

In some embodiments, the 5-(halomethyl)furfural is 5-(chloromethyl)furfural (CMF). For example, CMF may be converted into dimethylfuran and ethoxymethylfurfural. In other embodiments, the 5-(halomethyl)furfural is 5-(bromomethyl)furfural (BMF).

In some aspects, provided is a method of producing an alkylfuran, comprising: converting 5-(halomethyl)furfural produced according to any of the methods described herein into an alkylfuran. Any suitable methods known in the art may be employed for this reaction. In one variation, provided is a method of producing 2,5-dimethylfuran, by: converting 5-(chloromethyl)furfural (CMF) produced according to any of the methods described herein into 2,5-dimethylfuran (DMF).

The DMF can be further converted into para-xylene using any suitable methods known in the art. For example, DMF may be converted into para-xylene by Diels-Alder cycloaddition of ethylene. See e.g., U.S. Pat. No. 8,314,267; WO 2009/110402. Thus, in certain aspects, provided is a method of producing para-xylene, by: converting 5-(chloromethyl) furfural (CMF) produced according to any of the methods described herein into 2,5-dimethylfuran (DMF); and combining the DMF with ethylene in the presence of any suitable catalysts, and optionally solvent, to produce para-xylene. In certain variations, any suitable catalysts and optionally solvent described in WO 2013/040514, US 2013/0245316, and WO 2014/043468 may be employed. For example, in one variation, provided is a method of producing para-xylene, by: converting 5-(chloromethyl)furfural (CMF) produced according to any of the methods described herein into 2,5-dimethylfuran (DMF); and combining the DMF with ethylene in the presence of a catalyst, and optionally solvent, to produce para-xylene.

The para-xylene can be further oxidized to produce terephthalic acid. Any suitable methods to produce terephthalic acid from para-xylene may be employed. Thus, in certain aspects, provided is a method of producing terephthalic acid, by: converting 5-(chloromethyl)furfural (CMF) produced according to any of the methods described herein into 2,5-dimethylfuran (DMF); combining the DMF with ethylene in the presence of any suitable catalysts, and optionally solvent, to produce para-xylene; and oxidizing the para-xylene to produce terephthalic acid.

The terephthalic acid is a precursor of polyethylene terephthalate (PET), which may be used to manufacture polyester fabrics. Any suitable methods to produce PET from terephthalic acid may be employed. Thus, in certain aspects, provided is a method of producing polyethylene terephthalate (PET), by: converting 5-(chloromethyl)furfural (CMF) produced according to any of the methods described herein into 2,5-dimethylfuran (DMF); combining the DMF with ethylene in the presence of any suitable catalysts, and optionally solvent, to produce para-xylene; oxidizing the para-xylene to produce terephthalic acid; and producing PET from the terephthalic acid. For example, in some variations, PET can be produced by polymerizing terephthalic acid and ethylene glycol to produce polyethylene terephthalate.

Further, one or more additional products may also be produced according to the methods described herein. For example, humins, levulinic acid, formic acid, furfural, gamma valerolactone, or fulvic acid, or any combinations or mixtures thereof, may be produced. The methods described herein can reduce or minimize the amount of such additional product(s) present in the reaction mixture. For example, in some embodiments, the reaction mixture has less than 30%, less than 25%, less than 20%, less than 15%, less than 10%, or less than 5% of the one or more additional products described above.

Yield, Conversion, Selectivity

The methods described herein produce 5-(halomethyl) furfural at commercially viable yields. The yield of a product takes into account the conversion of the starting materials into the product, and the selectivity for the product over other byproducts that may be formed.

The difference between yield, conversion and selectivity is explained in the examples provided below. For example, with respect to the conversion of glucose into CMF, the reaction can be generalized as follows, where "A" represents the moles of glucose; "B" represents the moles of CMF produced; and "a" and "b" are stoichiometric coefficients.

$$aA \rightarrow bB.$$

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A.

Selectivity is the stoichiometrically relative amount of product B produced from the converted amount of reactant A, as expressed as a percentage by the following equation:

$$\text{Selectivity}(\%) = \frac{Bf * \frac{a}{b}}{Ao - Af} * 100\%,$$

where $A_o$ is the starting moles of reactant A; $A_f$ is the final number of moles of reactant A; and $B_f$ is the number of moles of product B. In some embodiments where "a/b"=1, and the equation can be simplified to:

$$\text{Selectivity}(\%) = \frac{Bf}{Ao - Af} * 100\%.$$

It should be understood, however, that depending on the type of feedstock used, the selectivity may be based on the total number of C6 monosaccharides or monomeric units having six carbons atoms.

The yield of product B is the percentage of reactant A that is converted into product B, as expressed by the following equation:

Yield(%)=Conversion(%)*Selectivity(%)

In certain embodiments, the methods described herein have a 5-(halomethyl)furfural yield of at least 10%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 20% to 80%, between 30% to 80%, between 40% to 80%, between 50%-80%, or between 60%-80% by weight.

In certain embodiments, the methods described herein have a 5-(halomethyl)furfural selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

Compositions

Provided herein are also compositions that include the feedstocks, acids, and salts described herein. Thus, provided is a composition that includes: a feedstock, an acid, and a salt, wherein the acid is HX, wherein X is halo; and the composition has a [H⁺] less than 12 M. In certain embodiments, the acid is aqueous acid. In certain aspects, provided is a composition that includes: feedstock, wherein the feedstock comprises C6 saccharides; hydrochloric acid; lithium chloride or calcium chloride, or a combination thereof; wherein the composition has a [H⁺] between 0.5 M and 9 M, and a [Cl⁻] between 5M and 20 M. In other aspects, provided is a composition that includes: feedstock, wherein the feedstock comprises C6 saccharides; hydrobromic acid; lithium bromide or calcium bromide, or a combination thereof; wherein the composition has a [H⁺] between 0.5 M and 9 M, and a [Cl⁻] between 5M and 20 M.

It should be understood that that any description of the feedstocks, acids, and salts described herein for the methods may be applied to the compositions the same as if each and every combination were individually listed.

For example, in some embodiments, the composition has a [H⁺] between 1 M and 6 M; between 1 M and 5 M; or between 2 M and 4 M. In some embodiments where 5-(chloromethyl)furfural is produced, the composition has a [Cl⁻] of about 12 M. In some embodiments where 5-(bromomethyl)furfural is produced, the composition has a [Br⁻] of about 12 M.

The composition may further include a solvent system. The solvent system may include, for example, one or more alkyl phenyl solvents, one or more heavy alkane solvents, one or more ester solvents, one or more aromatic solvents, one or more silicone oils, or any combinations or mixtures thereof, as described above. In certain embodiments of the composition, the solvent system includes one or more linear alkyl benzenes as described herein. In one embodiment of the composition, the solvent system includes toluene, other alkyl benzenes (e.g., Wibaryl® A, Wibaryl® B, Wibaryl® AB, Wibaryl® F, Wibaryl® R, Cepsa Petrepar® 550-Q, Cepsa Petrepar® 900-Q, Santovac® 5, Santovac® 7, Marlican®, Synnaph AB 3, Synnaph AB4), sulfolane, hexadecane, heptadecane, octadecane, icosane, heneicosane, docosane, tricosane, tetracosane, or any combinations or mixtures thereof.

In some embodiments of the composition, the feedstock is selected from corn stover, corn kernel, corn cob, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, saw dust, saw dust pellets, forest thinnings, slash, miscanthus, switchgrass, sorghum, bagasse, whole cane, empty palm fruit bunches, palm frond, beet pulp, beet process rafinate, manure, wastewater biosolids, green waste, agriculture residues, and food or feed processing residues, or any combinations thereof.

The composition may further include one or more additional compounds. For example, the compositions may further include humins, levulinic acid, formic acid, furfural, gamma valerolactone, or fulvic acid, or any combinations or mixtures thereof. In certain embodiments, the composition has less than 30%, less than 25%, less than 20%, less than 15%, less than 10%, or less than 5% of the one or more additional compounds described above.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−5%.

It should also be understood that reference to "between" two values or parameters herein includes (and describes) embodiments that include those two values or parameters per se. For example, description referring to "between x and y" includes description of "x" and "y" per se.

ENUMERATED EMBODIMENTS

The following enumerated embodiments are representative of some aspects of the invention.
1. A method for producing 5-(halomethyl)furfural, comprising:
    a) combining a feedstock, an aqueous acid, and a salt in a reaction vessel to form a reaction mixture, wherein: the aqueous acid is a halogen-containing acid; and the reaction mixture has a [$H^+$] concentration less than 12 M; and
    b) converting at least a portion of the feedstock in the reaction mixture to produce 5-(halomethyl)furfural.
2. The method of embodiment 1, wherein the salt has formula $A^{r+}(X^-)_r$, where $A^{r+}$ is a cation having charge r, and $X^-$ is an anion, and wherein the reaction mixture further has a [$X^-$] concentration between 2 M to 25 M.
3. The method of embodiment 2, wherein X is halo.
4. The method of any one of embodiments 1 to 3, further comprising isolating the 5-(halomethyl)furfural from the reaction mixture.
5. The method of any one of embodiments 1 to 4, wherein at least a portion of the feedstock is converted to 5-(halomethyl)furfural at a reaction temperature of at least 80° C.
6. The method of embodiment 5, wherein the reaction temperature is between 110° C. to 250° C.
7. The method of any one of embodiments 1 to 6, wherein the reaction mixture has a [$H^+$] concentration less than 10 M.
8. The method of embodiment 7, wherein the reaction mixture has a [$H^+$] concentration between 0.25 M to 10 M.
9. The method of embodiment 8, wherein the reaction mixture has a [$H^+$] concentration between 0.5 M and 6 M.
10. The method of any one of embodiments 1 to 9, wherein the aqueous acid is hydrochloric acid or hydrobromic acid.
11. The method of any one of embodiments 1 to 10, wherein the aqueous acid has a concentration less than 10 M.
12. The method of embodiment 11, wherein the aqueous acid has a concentration between 0.25 M to 10 N.
13. The method of any one of embodiments 1 to 12, wherein the salt comprises a monovalent or divalent cation.
14. The method of any one of embodiments 1 to 12, wherein the salt is a lithium salt or a calcium salt.
15. The method of any one of embodiments 1 to 12, wherein the salt is LiCl.
16. The method of any one of embodiments 1 to 15, wherein the feedstock, aqueous acid and salt are further combined with a solvent system.
17. The method of embodiment 16, wherein the solvent system comprises one or more alkyl phenyl solvents, one or more heavy alkane solvents, one or more ester solvents, one or more aromatic solvents, one or more silicone oils, or any combinations or mixtures thereof.
18. The method of embodiment 16, wherein the solvent system has a dipole moment less than 20.1 D.
19. The method of embodiment 16, wherein the solvent system comprises a hydrocarbon, halogenated hydrocarbon, ether, halogenated ether, cyclic ether, amide, silicon oil, or any combination or mixtures thereof.
20. The method of embodiment 16, wherein the solvent system comprises one or more linear alkyl benzenes.
21. The method of embodiment 16, wherein the solvent system comprises toluene, dodecylbenzene, pentylbenzene, hexylbenzene, Wibaryl®, Wibaryl® F, Wibaryl® A, Wibaryl® B, Wibaryl® AB, Wibaryl® R, Cepsa Petrepar® 500-Q, Cepsa Petrepar® 550-Q, Cepsa Petrene® 900-Q, Marlican®, Synnaph AB 3, Synnaph AB4, sulfolane, hexadecane, heptadecane, octadecane, icosane, heneicosane, docosane, tricosane, tetracosane, Santovac®-5, or any combinations or mixtures thereof.
22. The method of any one of embodiments 1 to 21, wherein the solvent has a boiling point of at least 110° C.
23. The method of any one of embodiments 1 to 22, wherein the feedstock is selected from the group consisting of corn stover, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinings, slash, miscanthus, switchgrass, sorghum, bagasse, manure, wastewater biosolids, green waste, and food or feed processing residues, or any combinations thereof.
24. The method of any one of embodiments 1 to 23, wherein the feedstock comprises glucose, fructose, sucrose, starch, inulin, cellulose, hemicellulose, cellulosic oligomers, cellobiose, or any combinations thereof.
25. The method of any one of embodiments 1 to 24, wherein the converting of at least a portion of the feedstock in the reaction mixture produces a product mixture, wherein the product mixture comprises an aqueous phase and an organic phase, wherein the aqueous phase and the organic phase each independently comprises 5-(halomethyl)furfural.

26. The method of any one of embodiments 1 to 25, wherein the mass to volume ratio of feedstock to solvent is between 1 g to 30 g feedstock per 100 mL solvent system.

27. The method of any one of embodiments 1 to 26, wherein at least 70% of the feedstock is converted at a reaction temperature greater than 140° C. to 5-(halomethyl)furfural in 20 minutes or less.

28. The method of any one of embodiments 1 to 26, wherein at least 50% of the feedstock is converted at reaction temperature greater than 170° C. to 5-(halomethyl)furfural in 10 minutes or less.

29. The method of any one of embodiments 1 to 28, wherein the reaction mixture further comprises one or more additional products selected from the group consisting of humins, levulinic acid, formic acid, furfural, gamma valerolactone, and fulvic acid.

30. The method of embodiment 29, wherein the reaction mixture has less than 30% of the one or more additional products.

31. The method of any one of embodiments 1 to 30, wherein the 5-(halomethyl)furfural is 5-(chloromethyl)furfural or 5-(bromomethyl)furfural.

32. The method of embodiment 1, wherein the feedstock is an aldose, and the reaction mixture has a [H$^+$] concentration less than 12 M.

33. The method of embodiment 32, wherein the feedstock is glucose, or a dimer or polymer thereof, or an isomer thereof.

34. The method of embodiment 1, wherein the feedstock is a ketose, and the reaction mixture has a [H$^+$] concentration less than 6 M.

35. The method of embodiment 34, wherein the feedstock is fructose, or a dimer or polymer thereof, or an isomer thereof.

36. A composition comprising:
    a feedstock,
    an aqueous acid, wherein the aqueous acid is a halogen-containing acid, and
    a salt,
    wherein the composition has a [H$^+$] concentration less than 12 M.

37. The composition of embodiment 36, wherein the salt has formula $A^{r+}(X^-)_r$, where $A^{r+}$ is a cation having charge r, and $X^-$ is an anion, and wherein the composition further has a [X$^-$] concentration between 2 M to 25 M.

38. The composition of embodiment 37, wherein X is halo.

39. The composition of any one of embodiments 36 to 38, wherein the composition has a [H$^+$] concentration less than 10 M.

40. The composition of embodiment 39, wherein the composition has a [H$^+$] concentration between 0.25 M to 10 M.

41. The composition of embodiment 40, wherein the composition has a [H$^+$] concentration between 0.5 M and 6 M.

42. The composition of any one of embodiments 36 to 41, wherein the aqueous acid is hydrochloric acid or hydrobromic acid.

43. The composition of any one of embodiments 36 to 42, wherein the aqueous acid has a concentration less than 10 M.

44. The composition of embodiment 43, wherein the aqueous acid has a concentration between 0.25 M to 10 M.

45. The composition of any one of embodiments 36 to 44, wherein the salt comprises a monovalent or divalent cation.

46. The composition of any one of embodiments 36 to 44, wherein the salt is a lithium salt or a calcium salt.

47. The composition of any one of embodiments 36 to 44, wherein the salt is LiCl.

48. The composition of any one of embodiments 36 to 47, wherein the composition further comprises a solvent system.

49. The composition of embodiment 48, wherein the solvent system comprises one or more alkyl phenyl solvents, one or more heavy alkane solvents, one or more ester solvents, one or more aromatic solvents, one or more silicone oils, or any combinations or mixtures thereof.

50. The composition of embodiment 48, wherein the solvent system has a dipole moment less than 20.1 D.

51. The composition of embodiment 48, wherein the solvent system comprises a hydrocarbon, halogenated hydrocarbon, ether, halogenated ether, cyclic ether, amide, silicon oil, or any combination or mixtures thereof.

52. The composition of embodiment 48, wherein the solvent system comprises one or more linear alkyl benzenes.

53. The composition of embodiment 48, wherein the solvent system comprises toluene, dodecylbenzene, pentylbenzene, hexylbenzene, Wibaryl®, Wibaryl® F, Wibaryl® A, Wibaryl® B, Wibaryl® AB, Wibaryl® R, Cepsa Petrepar® 500-Q, Cepsa Petrepar® 550-Q, Cepsa Petrene® 900-Q, Marlican®, Synnaph AB 3, Synnaph AB4, sulfolane, hexadecane, heptadecane, octadecane, icosane, heneicosane, docosane, tricosane, tetracosane, Santovac®-5, or any combinations or mixtures thereof.

54. The composition of any one of embodiments 48 to 53, wherein the solvent has a boiling point of at least 110° C.

55. The composition of any one of embodiments 36 to 54, wherein the feedstock is selected from the group consisting of corn stover, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinings, slash, miscanthus, switchgrass, sorghum, bagasse, manure, wastewater biosolids, green waste, and food or feed processing residues, or any combinations thereof.

56. The composition of any one of embodiments 36 to 55, wherein the feedstock comprises glucose, fructose, sucrose, starch, inulin, cellulose, hemicellulose, cellulosic oligomers, cellobiose, or any combinations thereof.

57. The composition of any one of embodiments 36 to 56, wherein the composition further comprises one or more additional products selected from the group consisting of humins, levulinic acid, formic acid, furfural, gamma valerolactone, and fulvic acid.

58. The composition of embodiment 57, wherein the composition has less than 30% of the one or more additional products.

59. The composition of any one of embodiments 36 to 58, wherein the 5-(halomethyl)furfural is 5-(chloromethyl)furfural or 5-(bromomethyl)furfural.

60. The composition of embodiment 36, wherein the feedstock is an aldose, and the reaction mixture has a [H$^+$] concentration less than 12 M.

61. The composition of embodiment 60, wherein the feedstock is glucose, or a dimer or polymer thereof, or an isomer thereof.

62. The composition of embodiment 36, wherein the feedstock is a ketose, and the reaction mixture has a [H$^+$] concentration less than 6 M.
63. The method of embodiment 62, wherein the feedstock is fructose, or a dimer or polymer thereof, or an isomer thereof.
64. A method for producing 5-(halomethyl)furfural, comprising:
   a) combining a feedstock, an acid, and a salt in a reaction vessel to form a reaction mixture, wherein:
   the acid is HX, wherein X is halo;
   the feedstock comprises one or more C6 monosaccharides, or the feedstock is a disaccharide or polysaccharide comprising monomeric units having six carbon atoms;
   the salt is LiX or CaX$_2$, or a combination thereof; and
   the reaction mixture has a [H$^+$] less than 12 M; and
   b) converting at least a portion of the feedstock in the reaction mixture into 5-(halomethyl)furfural.
65. The method of embodiment 64, wherein the reaction mixture has a [H$^+$] less than 8 M.
66. The method of embodiment 64, wherein the reaction mixture has a [H$^+$] between 0.5 M and 8 M.
67. The method of embodiment 64, wherein the reaction mixture has a [H$^+$] between 0.5 M and 6 M.
68. The method of embodiment 64, wherein the reaction mixture has a [H$^+$] between 1 M and 5 M.
69. The method of embodiment 64, wherein the reaction mixture has a [H$^+$] between 2 M and 4 M.
70. The method of any one of embodiments 64 to 69, wherein the reaction mixture has a [X$^-$] of at least 5 M.
71. The method of any one of embodiments 64 to 69, wherein the reaction mixture has a [X$^-$] of at least 7 M.
72. The method of any one of embodiments 64 to 69, wherein the reaction mixture has a [X-] of about 8 M.
73. The method of any one of embodiments 64 to 69, wherein the reaction mixture has a [X–] of about 12 M.
74. The method of any one of embodiments 64 to 73, wherein X is chloro or bromo.
75. The method of any one of embodiments 64 to 74, wherein the 5-(halomethyl)furfural is produced with a selectivity of at least 30%, wherein the selectivity is based on the total number of C6 monosaccharides or monomeric units having six carbons atoms.
76. The method of embodiment 75, wherein the selectivity is at least 40%.
77. The method of any one of embodiments 64 to 76, wherein at least 50% of the C6 monosaccharides or monomeric units having six carbons atoms are converted into 5-(halomethyl)furfural in less than 12 hours.
78. The method of any one of embodiments 64 to 77, wherein the feedstock, the acid and the salt are further combined with a solvent system.
79. The method of embodiment 78, wherein the solvent system comprises one or more alkyl phenyl solvents, one or more heavy alkane solvents, one or more ester solvents, one or more aromatic solvents, one or more silicone oils, or any combinations or mixtures thereof.
80. The method of embodiment 79, wherein the solvent system comprises one or more linear alkyl benzenes.
81. The method of embodiment 80, wherein the solvent system comprises para-xylene, mesitylene, naphthalene, anthracene, toluene, dodecylbenzene, pentylbenzene, hexylbenzene, sulfolane, hexadecane, heptadecane, octadecane, icosane, heneicosane, docosane, tricosane, tetracosane, or any combinations or mixtures thereof.
82. The method of embodiment 78, wherein the solvent system comprises one or more phenyl ether solvents.
83. The method of any one of embodiments 64 to 82, wherein the feedstock is selected from the group consisting of corn stover, corn cob, corn kernel, rice flour, whole cane, beet pulp, beet processing raffinate, empty palm fruit bunches, palm fronds, saw dust, wood pellets, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinnings, slash, miscanthus, switchgrass, sorghum, bagasse, manure, wastewater biosolids, green waste, and food or feed processing residues, or any combinations thereof.
84. The method of any one of embodiments 64 to 83, wherein the acid is produced in situ.
85. The method of any one of embodiments 64 to 84, wherein the salt is produced in situ.
86. A composition comprising:
   a feedstock, wherein the feedstock comprises one or more C6 monosaccharides, or the feedstock is a disaccharide or polysaccharide comprising monomeric units having six carbon atoms;
   an acid of formula HX, wherein X is halo; and
   a salt of formula LiX or CaX$_2$, or a combination thereof;
   wherein the composition has a [H$^+$] less than 12M.
87. The composition of embodiment 86, wherein the composition has a [H$^+$] less than 8 M.
88. The composition of embodiment 86, wherein the composition has a [H$^+$] between 0.5 M and 8 M.
89. The composition of embodiment 86, wherein the composition has a [H$^+$] between 0.5 M and 6 M.
90. The composition of embodiment 86, wherein the composition has a [H$^+$] between 1 M and 5 M.
91. The composition of embodiment 86, wherein the composition has a [H$^+$] between 2 M and 4 M.
92. The composition of any one of embodiments 86 to 91, wherein the composition has a [X$^-$] of at least 5 M.
93. The composition of any one of embodiments 86 to 91, wherein the composition has a [X$^-$] of at least 7 M.
94. The composition of any one of embodiments 86 to 91, wherein the composition has a [X–] of about 8 M.
95. The composition of any one of embodiments 86 to 91, wherein the composition has a [X–] of about 12 M.
96. The composition of any one of embodiments 86 to 95, wherein X is chloro or bromo.
97. The composition of any one of embodiments 86 to 96, further comprising a solvent system.
98. The composition of embodiment 97, wherein the solvent system comprises one or more alkyl phenyl solvents, one or more heavy alkane solvents, one or more ester solvents, one or more aromatic solvents, one or more silicone oils, or any combinations or mixtures thereof.
99. The composition of embodiment 97, wherein the solvent system comprises one or more linear alkyl benzenes.
100. The composition of embodiment 97, wherein the solvent system comprises para-xylene, mesitylene, naphthalene, anthracene, toluene, dodecylbenzene, pentylbenzene, hexylbenzene, sulfolane, hexadecane, heptadecane, octadecane, icosane, heneicosane, docosane, tricosane, tetracosane, or any combinations or mixtures thereof.
101. The composition of embodiment 97, wherein the solvent system comprises one or more phenyl ether solvents.
102. The composition of any one of embodiments 86 to 101, wherein the feedstock is selected from the group consisting of corn stover, corn cob, corn kernel, rice flour, whole cane, beet pulp, beet processing raffinate, empty palm fruit bunches, palm fronds, saw dust, wood pellets, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinnings, slash, miscanthus, switchgrass, sorghum, bagasse, manure, wastewater biosolids, green waste, and food or feed processing residues, or any combinations thereof.

103. A method for producing 5-(halomethyl)furfural, comprising:
    a) combining a feedstock, an acid, and a salt in a reaction vessel to form a reaction mixture, wherein:
    the acid is HX, wherein X is halo;
    the salt is $A^{r+}(X^-)_r$, wherein:
        $A^{r+}$ is a Group I or Group II cation, and
        $X^-$ is an halo anion; and
    the reaction mixture has a $[H^+]$ greater than 0 M and less than 12 M; and
    b) converting at least a portion of the feedstock in the reaction mixture into 5-(halomethyl)furfural.

104. The method of embodiment 103, wherein the reaction mixture has a $[H^+]$ greater than 0 M and less than or equal to 8 M.

105. The method of embodiment 103, wherein the reaction mixture has a $[H^+]$ greater than 0 M and less than or equal to 5 M.

106. The method of embodiment 103, wherein the reaction mixture has a $[H^+]$ between 0.5 M and 8 M.

107. The method of embodiment 103, wherein the reaction mixture has a $[H^+]$ greater than 0 M and less than or equal to 6 M.

108. The method of embodiment 103, wherein the reaction mixture has a $[H^+]$ between 0.5 M and 6 M.

109. The method of embodiment 103, wherein the reaction mixture has a $[H^+]$ between 1 M and 5 M.

110. The method of embodiment 103, wherein the reaction mixture has a $[H^+]$ between 2 M and 4 M.

111. The method of any one of embodiments 103 to 110, wherein the reaction mixture has a $[X^-]$ of at least 5 M.

112. The method of any one of embodiments 103 to 110, wherein the reaction mixture has a $[X^-]$ of at least 6 M.

113. The method of any one of embodiments 103 to 110, wherein the reaction mixture has a $[X^-]$ between 5 M and 12 M.

114. The method of any one of embodiments 103 to 110, wherein the reaction mixture has a $[X^-]$ between 6 M and 12 M.

115. The method of any one of embodiments 103 to 110, wherein the reaction mixture has a $[X^-]$ of at least 7 M.

116. The method of any one of embodiments 103 to 110, wherein the reaction mixture has a $[X-]$ of about 8 M.

117. The method of any one of embodiments 103 to 110, wherein the reaction mixture has a $[X-]$ of about 12 M.

118. The method of embodiment 103, wherein the reaction mixture has:
    a $[H^+]$ greater than 0 M and less than or equal to 8 M; and
    a $[X-]$ of at least 5 M.

119. The method of embodiment 103, wherein the reaction mixture has:
    a $[H^+]$ greater than 0 M and less than or equal to 8 M; and
    a $[X^-]$ of at least 10 M.

120. A method for producing 5-(halomethyl)furfural, comprising:
    a) combining a feedstock, an acid, and a salt in a reaction vessel to form a reaction mixture, wherein:
    the acid is HX, wherein X is halo;
    the salt is $A^{r+}(X^-)_r$, wherein:
        $A^{r+}$ is a Group I or Group II cation, and
        $X^-$ is an halo anion; and
    the reaction mixture has a $[H^+]$ greater than 0 M and less than or equal to 1 M; and
    b) converting at least a portion of the feedstock in the reaction mixture into 5-(halomethyl)furfural at a temperature of at least 115° C.

121. The method of embodiment 120, wherein the acid is added continuously to the reaction vessel.

122. The method of embodiment 120, wherein the reaction mixture has a $[H^+]$ greater than 0 M and less than 0.6 M.

123. The method of any one of embodiments 120 to 122, wherein the temperature of at least 130° C.

124. A method for producing 5-(halomethyl)furfural, comprising:
    a) combining a feedstock, an acid, and a salt in a reaction vessel to form a reaction mixture, wherein:
    the acid is HX, wherein X is halo;
    the salt is $A^{r+}(X^-)_r$, wherein:
        $A^{r+}$ is a Group I or Group II cation, and
        $X^-$ is an halo anion; and
    the reaction mixture has a $[H^+]$ greater than 0 M and less than 12 M; and
    the feedstock and the $[H^+]$ is present in the reaction mixture at a molar ratio of 1:1; and
    b) converting at least a portion of the feedstock in the reaction mixture into 5-(halomethyl)furfural.

125. A method for producing 5-(halomethyl)furfural, comprising:
    a) combining a feedstock, an acid, and a salt in a reaction vessel to form a reaction mixture, wherein:
    the acid is HX, wherein X is halo;
    the salt is $A^{r+}(X^-)_r$, wherein:
        $A^{r+}$ is a Group I or Group II cation, and
        $X^-$ is an halo anion; and
    the reaction mixture has a $[H^+]$ between the feedstock concentration and 5 M; and
    b) converting at least a portion of the feedstock in the reaction mixture into 5-(halomethyl)furfural at a temperature of at least 110° C.

126. The method of embodiment 125, wherein the temperature is at least 135° C.

127. The method of embodiment 125, wherein:
    the reaction mixture has a $[H^+]$ between the feedstock concentration and 2 M; and
    the temperature is at least 135° C.

128. The method of embodiment 125, wherein the reaction mixture has a $[H^+]$ between 0.1 times the feedstock concentration and 5 M.

129. A method for producing 5-(halomethyl)furfural, comprising:
    a) combining a feedstock, an acid, and a salt in a reaction vessel to form a reaction mixture, wherein:
    the acid is HX, wherein X is halo;
    the acid is continuously added; and
    the salt is $A^{r+}(X^-)_r$, wherein:
        $A^{r+}$ is a Group I or Group II cation, and
        $X^-$ is an halo anion; and b) converting at least a portion of the feedstock in the reaction mixture into 5-(halomethyl)furfural at a temperature of at least 110° C.

130. The method of embodiment 129, wherein the acid is continuously added at a rate to maintain an average [H$^+$] greater than 0 M.

131. The method of embodiment 129, wherein the acid is added continuously at a rate such that the [H$^+$] is greater than 0 M and less than 12 M.

132. The method of embodiment 129, wherein the acid is added continuously at a rate such that the [H$^+$] is greater than 0 M and less than or equal to 6 M.

133. The method of embodiment 129, wherein the acid is added continuously at a rate such that the [H$^+$] is greater than 0 M and less than or equal to the feedstock concentration.

134. The method of embodiments 103 to 133, wherein A$^{r+}$ is Li$^+$, Na$^+$, K$^+$, Rb$^+$, Cs$^+$, Mg$^{2+}$, Ca$^{2+}$, or Sr$^{2+}$.

135. The method of any one of embodiments 103 to 134, wherein X$^-$ is Cl$^-$ or Br$^-$.

136. A method for producing 5-(halomethyl)furfural, comprising:
a) combining a feedstock, an acid, and a salt in a reaction vessel to form a reaction mixture, wherein:
the acid is HX, wherein X is halo;
the salt comprises a Group I or Group II cation; and
the reaction mixture has a [H$^+$] greater than 0 M and less than 12 M; and
b) converting at least a portion of the feedstock in the reaction mixture into 5-(halomethyl)furfural.

137. The method of any one of embodiments 103 to 136, wherein the salt comprises Li$^+$, Na$^+$, K$^+$, Rb$^+$, Cs$^+$, Mg$^{2+}$, Ca$^{2+}$, or Sr$^{2+}$.

138. The method of any one of embodiments 103 to 136, wherein the salt comprises Li$^+$, Ca$^{2+}$, or Mg$^{2+}$.

139. The method of any one of embodiments 103 to 138, wherein salt is LiX, NaX, KX, RbX, CsX, MgX$_2$, CaX$_2$, or SrX$_2$.

140. The method of any one of embodiments 103 to 139, wherein X is Cl or Br.

141. The method of any one of embodiments 103 to 140, wherein the salt is LiCl, NaCl, KCl, RbCl, CsCl, MgCl$_2$, CaCl$_2$, SrCl$_2$, LiBr, NaBr, KBr, RbBr, CsBr, MgBr$_2$, CaBr$_2$, or SrBr$_2$.

142. The method of any one of embodiments 103 to 141, wherein the feedstock, acid, and salt are further combined with additional salt, wherein the additional salt is a silicate salt, a carbonate salt, a sulfate salt, a sulfide salt, a phosphate salt, a perchlorate salt, or a triflate salt.

143. The method of embodiment 142, wherein the additional salt is a triflate salt.

144. The method of embodiment 143, wherein the triflate salt is lithium triflate or sodium triflate.

145. A method for producing 5-(halomethyl)furfural, comprising:
converting a feedstock into 5-(halomethyl)furfural in the presence of (i) H$^+$, (ii) X$^-$, and (iii) a Group I or Group II cation, and wherein [H$^+$] is greater than 0 M and less than 12 M.

146. The method of embodiment 145, wherein [H$^+$] is greater than 0 M and less than or equal to 8 M.

147. The method of embodiment 145, wherein [H$^+$] is greater than 0 M and less than or equal to 5 M.

148. The method of embodiment 145, wherein [H$^+$] is between 0.5 M and 8 M.

149. The method of embodiment 145, wherein [H$^+$] is greater than 0 M and less than or equal to 6 M.

150. The method of embodiment 145, wherein [H$^+$] is between 0.5 M and 6 M.

151. The method of embodiment 145, wherein [H$^+$] is between 1 M and 5 M.

152. The method of embodiment 145, wherein [H$^+$] is between 2 M and 4 M.

153. The method of any one of embodiments 145 to 152, wherein [X$^-$] is at least 5 M.

154. The method of any one of embodiments 145 to 152, wherein [X$^-$] is at least 6 M.

155. The method of any one of embodiments 145 to 152, wherein [X$^-$] is between 5 M and 12 M.

156. The method of any one of embodiments 145 to 152, wherein [X$^-$] is between 6 M and 12 M.

157. The method of any one of embodiments 145 to 152, wherein [X$^-$] is at least 7 M.

158. The method of any one of embodiments 145 to 152, wherein [X–] is about 8 M.

159. The method of any one of embodiments 145 to 152, wherein [X–] is about 12 M.

160. The method of embodiment 145, wherein:
[H$^+$] is greater than 0 M and less than or equal to 8 M; and
[X$^-$] is at least 5M.

161. The method of embodiment 145, wherein:
[H$^+$] is greater than 0 M and less than or equal to 8 M; and
[X$^-$] is at least 10 M.

162. The method of any one of embodiments 103 to 161, wherein X is chloro or bromo.

163. The method of any one of embodiments 103 to 162, wherein the cation is Li$^+$, Na$^+$, K$^+$, Rb$^+$, Cs$^+$, Mg$^{2+}$, Ca$^{2+}$, or Sr$^{2+}$.

164. The method of embodiment 163, wherein the cation is Li$^+$, Mg$^{2+}$, or Ca$^{2+}$.

165. The method of any one of embodiments 103 to 164, wherein the 5-(halomethyl)furfural is produced with a selectivity of at least 30%, wherein the selectivity is based on the total number of C6 monosaccharides or monomeric units having six carbons atoms.

166. The method of embodiment 165, wherein the selectivity is at least 40%.

167. The method of any one of embodiments 103 to 166, wherein at least 50% of the C6 monosaccharides or monomeric units having six carbons atoms are converted into 5-(halomethyl)furfural in less than 12 hours.

168. The method of any one of embodiments 103 to 167, wherein the feedstock, the acid and the salt are further combined with a solvent system.

169. The method of embodiment 168, wherein the solvent system comprises one or more alkyl phenyl solvents, one or more heavy alkane solvents, one or more ester solvents, one or more aromatic solvents, one or more silicone oils, or any combinations or mixtures thereof.

170. The method of embodiment 169, wherein the solvent system comprises one or more linear alkyl benzenes.

171. The method of embodiment 169, wherein the solvent system comprises para-xylene, mesitylene, naphthalene, anthracene, toluene, dodecylbenzene, pentylbenzene, hexylbenzene, sulfolane, hexadecane, heptadecane, octadecane, icosane, heneicosane, docosane, tricosane, tetracosane, or any combinations or mixtures thereof.

172. The method of embodiment 169, wherein the solvent system comprises one or more phenyl ether solvents.

173. The method of any one of embodiments 103 to 172, wherein the feedstock comprises one or more C6 monosaccharides, disaccharides comprising monomeric units having six carbon atoms, or polysaccharides comprising monomeric units having six carbon atoms.

174. The method of any one of embodiments 103 to 172, wherein the feedstock is selected from the group consisting of corn stover, corn cob, corn kernel, rice flour, whole cane, beet pulp, beet processing raffinate, empty palm fruit bunches, palm fronds, saw dust, wood pellets, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinnings, slash, miscanthus, switchgrass, sorghum, bagasse, manure, wastewater biosolids, green waste, and food or feed processing residues, or any combinations thereof.

175. The method of any one of embodiments 103 to 172, wherein the feedstock comprises cellulose, glucose, fructose, or any combinations thereof.

176. The method of any one of embodiments 103 to 175, wherein the acid is produced in situ.

177. The method of any one of embodiments 103 to 176, wherein the salt is produced in situ.

178. A composition comprising:
a feedstock;
an acid of formula HX, wherein X is halo; and
a salt of formula $A'^{+}(X^{-})_{r}$, wherein:
$A'^{+}$ is a Group I or Group II cation, and
$X^{-}$ is an halo anion; and
wherein the composition has a $[H^{+}]$ greater than 0 M and less than 12M.

179. The composition of embodiment 178, wherein the composition has a $[H^{+}]$ greater than 0 M and less than or equal to 8 M.

180. The composition of embodiment 178, wherein the composition has a $[H^{+}]$ greater than 0 M and less than or equal to 5 M.

181. The composition of embodiment 178, wherein the composition has a $[H^{+}]$ between 0.5 M and 8 M.

182. The composition of embodiment 178, wherein the composition has a $[H^{+}]$ greater than 0 M and less than or equal to 6 M.

183. The composition of embodiment 178, wherein the composition has a $[H^{+}]$ between 0.5 M and 6 M.

184. The composition of embodiment 178, wherein the composition has a $[H^{+}]$ between 1 M and 5 M.

185. The composition of embodiment 178, wherein the composition has a $[H^{+}]$ between 2 M and 4 M.

186. The composition of any one of embodiments 178 to 185, wherein the composition has a $[X^{-}]$ of at least 5 M.

187. The composition of any one of embodiments 178 to 185, wherein the composition has a $[X^{-}]$ of at least 6 M.

188. The composition of any one of embodiments 178 to 185, wherein the composition has a $[X^{-}]$ between 5 M and 12 M.

189. The composition of any one of embodiments 178 to 185, wherein the composition has a $[X^{-}]$ between 6 M and 12 M.

190. The composition of any one of embodiments 178 to 185, wherein the composition has a $[X^{-}]$ of at least 7 M.

191. The composition of any one of embodiments 178 to 185, wherein the composition has a $[X-]$ of about 8 M.

192. The composition of any one of embodiments 178 to 185, wherein the composition has a $[X-]$ of about 12 M.

193. The composition of embodiment 178, wherein the composition has:
a $[H^{+}]$ greater than 0 M and less than or equal to 8 M; and
a $[X-]$ of at least 5 M.

194. The composition of embodiment 178, wherein the composition has:
a $[H^{+}]$ greater than 0 M and less than or equal to 8 M; and
a $[X-]$ of at least 10 M.

195. The composition of any one of embodiments 178 to 194, wherein X is chloro or bromo.

196. The composition of any one of embodiments 178 to 194, wherein $A'^{+}$ is $Li^{+}$, $Na^{+}$, $K^{+}$, $Rb^{+}$, $Cs^{+}$, $Mg^{2+}$, $Ca^{2+}$, or $Sr^{2+}$.

197. The composition of any one of embodiments 178 to 194, wherein the salt comprises $Li^{+}$, $Na^{+}$, $K^{+}$, $Rb^{+}$, $Cs^{+}$, $Mg^{2+}$, $Ca^{2+}$, or $Sr^{2+}$.

198. The composition of any one of embodiments 178 to 194, wherein the salt comprises $Li^{+}$, $Ca^{2+}$, or $Mg^{2+}$.

199. The composition of any one of embodiments 178 to 194, wherein salt is LiX, NaX, KX, RbX, CsX, $MgX_2$, $CaX_2$, or $SrX_2$.

200. The composition of any one of embodiments 178 to 194, wherein the salt is LiCl, NaCl, KCl, RbCl, CsCl, $MgCl_2$, $CaCl_2$, $SrCl_2$, LiBr, NaBr, KBr, RbBr, CsBr, $MgBr_2$, $CaBr_2$, or $SrBr_2$.

201. The composition of any one of embodiments 178 to 200, further comprising an additional salt, wherein the additional salt is a silicate salt, a carbonate salt, a sulfate salt, a sulfide salt, a phosphate salt, a perchlorate salt, or a triflate salt.

202. The composition of embodiment 201, wherein the additional salt is a triflate salt.

203. The composition of embodiment 202, wherein the triflate salt is lithium triflate or sodium triflate.

204. The composition of any one of embodiments 178 to 203, further comprising a solvent system.

205. The composition of embodiment 204, wherein the solvent system comprises one or more alkyl phenyl solvents, one or more heavy alkane solvents, one or more ester solvents, one or more aromatic solvents, one or more silicone oils, or any combinations or mixtures thereof.

206. The composition of embodiment 204, wherein the solvent system comprises one or more linear alkyl benzenes.

207. The composition of embodiment 204, wherein the solvent system comprises para-xylene, mesitylene, naphthalene, anthracene, toluene, dodecylbenzene, pentylbenzene, hexylbenzene, sulfolane, hexadecane, heptadecane, octadecane, icosane, heneicosane, docosane, tricosane, tetracosane, or any combinations or mixtures thereof.

208. The composition of embodiment 204, wherein the solvent system comprises one or more phenyl ether solvents.

209. The composition of any one of embodiments 178 to 208, wherein the feedstock comprises one or more C6 monosaccharides, disaccharides comprising monomeric units having six carbon atoms, or polysaccharides comprising monomeric units having six carbon atoms.

210. The composition of any one of embodiments 178 to 208, wherein the feedstock is selected from the group consisting of corn stover, corn cob, corn kernel, rice flour, whole cane, beet pulp, beet processing raffinate, empty palm fruit bunches, palm fronds, saw dust, wood pellets, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips, forest thinnings, slash, miscanthus, switchgrass, sorghum, bagasse, manure, wastewater biosolids, green waste, and food or feed processing residues, or any combinations thereof.

211. The composition of any one of embodiments 178 to 208, wherein the feedstock comprises cellulose, glucose, fructose, or any combinations thereof.

212. A method of producing 2,5-dimethylfuran, comprising:
producing 5-(halomethyl)furfural according to the method of any one of embodiments 1 to 35, 63 to 85, and 103 to 177; and
converting the 5-(halomethyl)furfural into 2,5-dimethylfuran.

213. A method of producing para-xylene, comprising:
producing 5-(halomethyl)furfural according to the method of any one of embodiments 1 to 35, 63 to 85, and 103 to 177;
converting the 5-(halomethyl)furfural into 2,5-dimethylfuran; and
combining the 2,5-dimethylfuran and ethylene to produce para-xylene.

214. A method of producing terephthalic acid, comprising:
producing 5-(halomethyl)furfural according to the method of any one of embodiments 1 to 35, 63 to 85, and 103 to 177;
converting the 5-(halomethyl)furfural into 2,5-dimethylfuran;
combining the 2,5-dimethylfuran and ethylene to produce para-xylene; and
oxidizing the para-xylene to produce terephthalic acid.

215. A method of producing polyethylene terephthalate, comprising:
producing 5-(halomethyl)furfural according to the method of any one of embodiments 1 to 35, 63 to 85, and 103 to 177;
converting the 5-(halomethyl)furfural into 2,5-dimethylfuran;
combining the 2,5-dimethylfuran and ethylene to produce para-xylene;
oxidizing the para-xylene to produce terephthalic acid; and
polymerizing terephthalic acid and ethylene glycol to produce polyethylene terephthalate.

EXAMPLES

The following Examples are merely illustrative and are not meant to limit any aspects of the present disclosure in any way.

In the Examples described below, it should be understood that the temperatures indicated are bath temperatures, unless otherwise stated. Further, in the Examples below that the reaction temperature may be up to 20% lower than the bath temperature.

Example 1

Effect of Varying [H$^+$]

This Example demonstrates the effect varying the [H$^+$] concentration on the production of CMF from glucose. An aqueous solution with [H$^+$] and [Li$^+$] specified in Table 1 below and a constant 12 M [Cl$^-$] was prepared for each reaction in this Example.

To a 500 mL round bottom flask equipped with a stir bar was added 40-41 mL of an acidic lithium chloride brine solution and 4.0-4.1 g of glucose. The glucose was then allowed to dissolve in the aqueous solution at room temperature and a 0.1-1 mL sample of the aqueous solution was removed for glucose concentration analysis. 80 ml of toluene was then added to the reaction flask, and the flask was sealed. The reaction mixture was then stirred in a preheated 150° C. oil bath for 15-16 min. The reaction was then removed from heat and cooled using an ice water bath.

The cooled reaction mixture was filtered. The retained solids were then washed with small aliquots of toluene resulting in a total toluene wash of 200 mL. The solids were also washed into a separate catch-flask with small aliquots of water for a total of 200 mL, which was then diluted to 250 mL for sugar analysis, and the solids were dried overnight in a 119° C. oven. The biphasic reaction mixture and combined toluene wash were then separated in a 250 mL separatory funnel. The aqueous phase was emptied into a graduated cylinder to determine the total aqueous volume post reaction. Two dilutions were then prepared from the recovered aqueous where an aliquot was diluted in water for sugar analysis by HPLC (40×-100× dilution depending on the reaction) and an aliquot was diluted in tetrahydrofuran and a small amount of concentrated hydrochloric acid (depending on lithium chloride concentration) such that the resulting mixture was observed to be homogeneous for CMF analysis by HPLC (40× dilution). The combined organics were dried over sodium sulfate, filtered, and diluted using toluene (250 mL-500 mL depending on reaction). A serial dilution was then prepared for HPLC by removing a small aliquot from the bulk organic sample and diluting with toluene to a measured volume (5×-20× dilution depending on reaction).

The conversion, as well as CMF yield and selectivity for each of the reactions performed in this Example are summarized in Table 1 below.

TABLE 1

| No. | [H+] | [Li+] | Conv. Glucose (%) | Yield CMF (%) | Selec. CMF (%) |
|---|---|---|---|---|---|
| 1 | 0M | 12M | 7 | 0 | 0 |
| 2 | 0.1M | 11.9M | 31.36 | 9.37 | 29.87 |
| 3 | 0.5M | 11.5M | 72.3 | 46.47 | 64.28 |
| 4* | 1M | 11M | 94.11 | 62.95 | 66.89 |
| 5 | 2M | 10M | 98.25 | 69.1 | 70.3 |
| 6 | 3M | 9M | 100 | 67.7 | 67.7 |
| 7** | 2M | 0M | 15.5 | 0.3 | 2.0 |

*Total volume was 87% greater (7.5 grams of glucose, 75 ml of aqueous, and 150 ml of toluene were used).
**No salt was added to this reaction ([Cl$^-$] was 2M)

The results in Table 1 above demonstrate that use of various [H$^+$] concentrations in the reaction mixture produces CMF with selectivity in the presence a salt such as LiCl.

Example 2

Effect of Varying Reaction Temperature

This Example demonstrates the effect of varying the reaction temperature on the production of CMF from glucose.

To a 500 mL round bottomed flask was added an aqueous solution (40 mL), prepared by adding 15 mL of concentrated HCl into a stirring, cooled solution of 12 M LiCl in water. To the flask was then added glucose (4.0 g, 22 mmol), which was observed to dissolve at room temperature. A 1 mL aliquot was then taken and diluted to 100 mL in water for the sugar assay analysis. Toluene (80 mL) was then added to the flask and the flask was then sealed. The biphasic reaction mixture was then heated in an oil bath over the course of 8 minutes with stirring to the temperature specified in Table 2 below. The temperatures at each minute were recorded and summarized in Table 2 below.

TABLE 2

| Time (min) | Reaction 1 | Reaction 2 | Reaction 3 |
|---|---|---|---|
| 1 | 118.0° C. | 141.0° C. | 172.4° C. |
| 2 | 120.4° C. | 140.3° C. | 172.0° C. |
| 3 | 124.0° C. | 142.7° C. | 173.0° C. |
| 4 | 123.7° C. | 146.0° C. | 175.0° C. |
| 5 | 122.2° C. | 147.1° C. | 176.3° C. |
| 6 | 125.0° C. | 146.8° C. | 173.0° C. |
| 7 | 127.8° C. | 146.4° C. | 169.5° C. |
| 8 | 126.0° C. | 143.3° C. | 172.0° C. |

After 8 minutes, the reaction was removed from heat and cooled using a water bath. Ice was added to the water bath to help with cooling.

The cooled reaction mixture was filtered. The retained solids were then washed with small aliquots of toluene resulting in a total toluene wash of 200 mL. The solids were also washed into a separate flask with aliquots of water for a total of 200 mL, which was then diluted to 250 mL for the sugar assay analysis and the solids were dried overnight in an oven. The biphasic reaction mixture and combined toluene wash were then separated, and the aqueous phase was emptied into a graduated cylinder to determine the total aqueous volume post reaction. Two dilutions were then prepared from the recovered aqueous where an aliquot was diluted in water for sugar analysis on HPLC (40×-100× dilution depending on the reaction) and an aliquot was diluted in tetrahydrofuran and a small amount of concentrated hydrochloric acid (depending on lithium chloride concentration) such that the resulting mixture became homogeneous for CMF analysis for HPLC (40× dilution). The combined organics were dried over sodium sulfate, filtered, and diluted using toluene (250 mL-500 mL depending on reaction). A serial dilution was then prepared for HPLC by removing a small aliquot from the bulk organic sample and diluting with toluene to a measured volume (5×-20× dilution depending on reaction and expected concentration)

Sugars were analyzed by HPLC using a mobile phase of 10 mM sulfuric acid in water at a flow rate of 0.6 mL/min and temperature of 60° C. A refractive index detector was used for quantitation of sugars with glucose eluting at 10.5 minutes. Quantitation was performed by comparing peak areas of the sample to the peak area of a known glucose standard.

CMF was analyzed by HPLC using a normal phase column isocratically at a temperature of 50° C. The mobile phase was 4:1 hexane/THF flowing at 1.0 mL/min. A UV detector was used for quantitation of CMF with CMF eluting at 2.5 minutes. Quantitation of CMF was performed by comparing peak areas of the samples to the peak area of a known CMF standard.

The conversion, as well as CMF yield and selectivity for each of the reactions performed in this Example are summarized in Table 3 below.

TABLE 3

| No. | [H$^+$] (M) | [Li$^+$] (M) | [Cl$^-$] (M) | Temp. (° C.) | Conv. Glucose (%) | Yield CMF (%) |
|---|---|---|---|---|---|---|
| 1 | 1 | 11 | 12 | 125° C. | 30.07% | 6.47% |
| 2 | 1 | 11 | 12 | 145° C. | 38.5% | 18.6% |
| 3 | 1 | 11 | 12 | 175° C. | 89.6% | 55.11% |

Example 3

Partition Coefficient Screen

This Example demonstrates the effect of various solvents, salts and salt concentrations on the partition coefficient (PC) in a system with CMF.

To a 25 mL microwave vial was added 4 mL acidic brine solution and 4 mL organic solution, and 100 mg CMF to produce the phases described in Table 4 below. The microwave vial was sealed, and the mixture was shaken until all of the CMF was observed to be dissolved. A 1 mL sample was removed from each phase. The microwave vial was then resealed, and re-shaken.

The 1 mL samples were added to volumetric flasks, where the acidic brine solution was diluted with THF and an amount of 37% HCl (~3 mL) sufficient to eliminate the formation of a biphase with THF. The organic phase sample was diluted with toluene. The dilutions were then put into 1 dram vials and saved.

Further sampling of each phase was repeated every 2 hours for the duration of each 4-hour experiment resulting in a total of 6 samples per experiment. Throughout the course of the experiment the microwave vial was shaken every 20 minutes to promote contact between the two phases. The 6 samples of each experiment in this Example were then taken from the 1 dram vials and put into 1.5 ml vials and submitted to HPLC for CMF analysis.

Table 4 below summarizes the data for each of the experiments run in this Example, and provides the normalized ratio of CMF in the organic to aqueous phase,

TABLE 4

| No. | Organic Phase | Aqueous Phase | Temp (° C.) | Normalized ratio (organic:aqueous) | log PC |
|---|---|---|---|---|---|
| 1 | Toluene | HCl (11.66N) | 25 | 3.0 | 0.48 |
| 2 | Toluene | 1N H$^+$ 11N Li$^+$ 12N Cl$^-$ | 24.6 | 144.0 | 2.16 |
| 3 | Toluene | 6N H$^+$ 6N Li$^+$ 12N Cl$^-$ | 25 | 17.4 | 1.24 |
| 4 | Toluene | 2N H$^+$ 10N Li$^+$ 12N Cl$^-$ | 29.7 | 72.9 | 1.86 |
| 5 | Toluene | 1N H$^+$ 11N Li$^+$ 12N Cl$^-$ | 50 | 110.0 | 2.04 |
| 6 | Toluene | 6N H$^+$ 6N Li$^+$ 12N Cl$^-$ | 50 | 18.9 | 1.27 |
| 7 | Toluene | 2N H$^+$ 10N Li$^+$ 12N Cl$^-$ | 50 | 79.6 | 1.9 |
| 8 | Toluene | 2N H$^+$ 4N Mg$^{2+}$ 12N Cl$^-$ | 23.6 | 61.3 | 1.78 |
| 9 | Toluene | 2N H$^+$ 4M sodium triflate 2M Cl$^-$ | 27.1 | 8.3 | 0.92 |
| 10 | Toluene | 2M H$^+$ 10M Na$^+$ 12M Cl$^-$ | 24.6 | 66.1 | 1.82 |
| 11 | Toluene | 2M H$^+$ 1:1 12M LiCl:saturated NaCl | 24.1 | 90.1 | 1.95 |
| 12 | Toluene | 2M H$^+$ saturated KCl | 24.2 | 222.0 | 2.34 |
| 13 | Toluene | 2M H$^+$ 1:1 12M LiCl:saturated KCl | 24.8 | 71.1 | 1.85 |
| 14 | Toluene | 2M H$^+$ 1:2 12M LiCl:saturated NaCl | 24.5 | 100.0 | 2 |
| 15 | Toluene | 2M H$^+$ 1:2 12M LiCl:saturated KCl | 24.5 | 119.0 | 2.07 |
| 16 | Toluene | 2M H$^+$ 1:1 12M LiCl:saturated MgCl$_2$ | 22 | 68.0 | 1.83 |
| 17 | Toluene | 2M H$^+$ 10M Zn$^{2+}$ 24M Cl$^-$ | 22 | 0.6 | −0.23 |

TABLE 4-continued

| No. | Organic Phase | Aqueous Phase | Temp (° C.) | Normalized ratio (organic:aqueous) | log PC |
|---|---|---|---|---|---|
| 18 | Toluene | 2M H$^+$ 4.13M Ca$^{2+}$ 12.2M Cl$^-$ | 27 | 73.8 | 1.87 |
| 19 | Toluene | 2M H$^+$ 6M Ca$^{2+}$ 14M Cl$^-$ | 27 | 80.0 | 1.9 |
| 20 | Toluene | 2M H$^+$ 4.13M Ca$^{2+}$ 12.2M Cl– | 50 | 82.6 | 1.91 |
| 21 | Toluene | 2M H$^+$ 6M Ca$^{2+}$ 14M Cl$^-$ | 50 | 141.7 | 2.15 |
| 22 | Toluene | 2M H$^+$ Satd. Rb | 24.5 | 74.7 | 1.87 |
| 23 | Toluene | 2M H$^+$ Satd. Cs | 24.5 | 41.3 | 1.61 |
| 24 | Cepsa ® 550Q | 6N H$^+$ 6N Li$^+$ 12N Cl$^-$ | 23.3 | 1.6 | 1.61 |
| 25 | Cepsa ® 550Q | 1N H$^+$ 11N Li$^+$ 12N Cl$^-$ | 24.5 | 20.3 | 1.31 |
| 26 | Cepsa ® 900Q | 1N H$^+$ 11N Li$^+$ 12N Cl$^-$ | 22.8 | 10.2 | 1.01 |
| 27 | Cepsa ® 900Q | 6N H$^+$ 6N Li$^+$ 12N Cl$^-$ | 26.5 | 0.9 | −0.04 |
| 28 | Santovac ®-5 | 1N H$^+$ 11N Li$^+$ 12N Cl$^-$ | 27.2 | 60.7 | 1.78 |
| 29 | Santovac ®-5 | 6N H$^+$ 6N Li$^+$ 12N Cl$^-$ | 23.7 | 6.6 | 0.82 |
| 30 | Santovac ®-5 | 2N H$^+$ 10N Li$^+$ 12N Cl$^-$ | 28.1 | 43.7 | 1.64 |
| 31 | Santovac ®-5 | 1N H$^+$ 11N Li$^+$ 12N Cl$^-$ | 50 | 65.6 | 1.81 |
| 32 | Santovac ®-5 | 6N H$^+$ 6N Li$^+$ 12N Cl$^-$ | 50 | 10.3 | 1.01 |
| 33 | Santovac ®-5 | 2N H$^+$ 10N Li$^+$ 12N Cl$^-$ | 50 | 55.9 | 1.74 |
| 34 | Dichloroethane (4 mL) | 37% HCl (4 mL) | 28.5 | 10.9 | 1.03 |
| 35 | Dichloroethane (17.6 mL) | 37% HCl (4 mL) | 28.5 | 11.6 | 1.7 |

Example 4

Effect of Varying [Cl$^-$]

This Example demonstrates the effect of varying the chloride concentration (based on the salt added) on the production of CMF from glucose.

To a 200 nit round bottom flask equipped with a stir bar, 4.1 g of D-(+) glucose was added. 41 mL of 2M H+ and LiCl (in accordance with the [Li$^+$] set forth in Table 5A below) was added to the round bottom flask and placed on a stir plate allowing the mixture to stir at a moderate rate until all the glucose has visibly dissolved. A 1 mL aliquot was analyzed for HCl concentration, and the other 0.5 was diluted 100× with de-ionized water and analyzed for glucose concentration. To the LiCl/glucose solution, 80 mL of toluene was then added and the flask was sealed. The flask heated in a 110° C. oil bath and stirred for 60 minutes. The flask was then removed from the oil bath and placed in a water bath and allowed to cool to room temperature.

The cooled reaction mixture was filtered. The retained solids were then washed with small aliquots of toluene resulting in a total toluene wash of 200 mL. A sample of the filtrate was taken for glucose analysis. The contents of the toluene were transferred to a 250 mL separatory funnel. Two phases became visible in the separatory funnel. The lower aqueous phase was emptied into a 50 mL graduated cylinder. The organic fraction remaining in the funnel was isolated and dried over sodium sulfate. A sample of the aqueous phase was diluted with THF and 3 mL HCl, and analyzed for CMF concentration. Another sample of the aqueous phase was diluted with water, and analyzed for glucose concentration. The organic fraction was then filtered, washed with toluene, along with the sodium sulfate solids. A 1 sample was taken, diluted 10× with toluene in a 10 mL volumetric flask and analyzed for CMF concentration. All samples were saved in 1 dram vials and saved.

Glucose and CMF concentrations were analyzed according to the protocol described in Example 2 above. The conversion, as well as CMF yield and selectivity for each of the reactions performed in this Example are summarized in Table 5A below.

TABLE 5A

| No. | [Li+] (M) | [Cl−] (M) | Conv. Glucose (%) | Selectivity CMF (%) | Yield CMF (%) |
|---|---|---|---|---|---|
| 1 | 9 | 11 | 68.6 | 65.6 | 45.0 |
| 2 | 8 | 10 | 61.8 | 61.0 | 37.7 |
| 3 | 7 | 9 | 41.9 | 51.7 | 21.7 |

The experiments in this Example were repeated at a [H+] of 4M, and the amount of LiCl as set forth in the Table 5B below.

TABLE 5B

| [Li$^+$] | [Cl$^-$] | % Conversion Glucose | % Yield CMF | % Selectivity CMF |
|---|---|---|---|---|
| 0 | 4 | 21.25 | 1.47 | 7 |
| 4 | 8 | 56.35 | 19.71 | 34.98 |
| 6 | 10 | 87.61 | 48.17 | 54.98 |
| 8 | 12 | 97.8 | 60.6 | 62 |

Example 5

Effect of Varying Salts

This Example demonstrates the effect of various chloride salts on the production of CMF from glucose.

For reactions 1 to 4, to a round bottomed flask equipped with a stir bar was added the aqueous solution described in Table 6 below (40 mL). Glucose (at the amounts set forth in Table 6 below) was added to the flask and was allowed to stir at room temperature until the glucose was visibly observed to be dissolved. Depending on the homogeneity observed for the aqueous phase, a 1 mL sample was then removed and diluted to 10 mL in water for sugar analysis. Toluene (at the volume set forth in Table 6 below) was then added and the reaction flask was sealed. The reaction mixture was then heated to the temperature set forth in in Table 6 below and allowed to stir for 60 minutes (unless indicated otherwise below).

For reaction 1, after about 5 minutes, the aqueous layer was observed to be yellow. After about 10 minutes, the reaction mixture was observed to be dark red. After about 13.5 minutes, the reaction mixture was observed to be brown.

For reaction 2, after about 22 minutes, the aqueous and organic layers were observed to be mixed, and the reaction mixture was observed to be orange. After about 36 minutes, the aqueous and organic layer were observed to at least partially separate, and the organic phase was observed to be red.

For reaction 3, after about 5 minutes, the aqueous layer was observed to be yellow. After about 11 minutes, bubbles were observed in the reaction mixture, and the aqueous and organic layers were observed to be mixed. After about 13 minutes, the reaction mixture was observed to be brown. The reaction was stopped after 15 minutes.

For reaction 4, after about 4.3 minutes, the organic layer was observed to be green. After 6 minutes, the reaction mixture was observed to be dark brown. The reaction was stopped after 9 minutes.

For reaction 5, to a round bottomed flask was added the aqueous solution described in Table 6 above (40 ml). Glucose (at the amount set forth in Table 6 below) was added to the flask, and was allowed to stir at room temperature until the glucose was visibly observed to be dissolved. Lithium iodide (288 mg, 9.7 mol %) was then added to the flask, and was also allowed to stir at room temperature until the LiI was visibly observed to dissolve into the mixture (turned a light yellow color most likely due to iodine impurities). The reaction mixture was observed to turn a light yellow color. Toluene (at the volume set forth in Table 6 below) was then added to the flask, and the flask was sealed. The reaction mixture was heated to 110° C., and allowed to stir for 60 minutes. After about 4 minutes, the organic layer was observed to be a bright violet color. After about 15 minutes, the entire reaction mixture was observed to be a deep purple color. After about 60 minutes, the reaction mixture was observed to be a dark brown color, and solids were observed at the bottom of the flask. The flask was removed from heat, and cooled using an ice/water bath.

For reactions 1 to 5, the cooled reaction mixture was filtered. The retained solids were then washed with small aliquots of toluene resulting in a total toluene wash of 200 mL. The solids were also washed into a separate catch-flask with small aliquots of water for a total of 200 mL which was then diluted to 250 mL for sugar analysis, and the solids were dried overnight in a 119° C. oven. The biphasic reaction mixture and combined toluene wash were then separated in a 250 mL separatory funnel. The aqueous phase was emptied into a graduated cylinder to determine the total aqueous volume post reaction. Two dilutions were then prepared from the recovered aqueous where an aliquot was diluted in water for sugar analysis by HPLC (40×-100× dilution depending on the reaction) and an aliquot was diluted in tetrahydrofuran and a small amount of concentrated hydrochloric acid (depending on lithium chloride concentration) such that the resulting mixture became homogeneous for CMF analysis on HPLC (40× dilution). The combined organics were dried over sodium sulfate, filtered, and diluted using toluene (250 mL-500 mL depending on reaction). A serial dilution was then prepared for HPLC by removing a small aliquot from the bulk organic sample and diluting with toluene to a measured volume (5×-20× dilution depending on reaction and expected concentration).

TABLE 6

| No. | Glucose (g, mmol) | [H$^+$] (M) | Salt | Cation (M) | [Cl$^-$] (M) | Solvent (ml) | Temp. (° C.) | % Conv. Glucose | % Yield CMF | % Selec. CMF |
|---|---|---|---|---|---|---|---|---|---|---|
| 1 | 4.0435 g, 22.4 mmol | 2M | MgCl$_2$ | Mg$^{2+}$ (—)$^a$ | —$^a$ | Toluene (80 ml) | 150° C. | 46.60% | 12.70% | 27.20% |
| 2 | 3.9987 g, 22.2 mmol | 2M | NaCl | Na$^+$ (sat.) | sat. | Toluene (80 ml) | 110° C. | 21% | 4.30% | 20.50% |
| 3 | 2.2937 g, 12.7 mmol | 2M | Na(OTf) | Na$^+$ (sat.) | 2M | Toluene (46 ml) | 150° C. | 57.10% | 11.60% | 20.30% |
| 4 | 2.0267 g, 11.25 mmol | 2M | ZnCl$_2$ | Zn$^+$ (10M) | 22M | Toluene (41 ml) | 150° C. | 92.2% | 0 | 0 |
| 5 | 3.9949 g, 22.17 mmol | 2M | LiCl, LiI | Li$^+$ (12M) | 12M | Toluene (40 ml) | 110° C. | 86.8 | 31% | 35.7 |

$^a$concentration value not available

Example 6A-6C

Effect of Varying HCl Concentration on 5-(Chloromethyl)Furfural Production

These Examples demonstrate the effect of varying the HCl concentration on the yield and selectivity of CMF produced from glucose.

Example 6A

To a 500 ml round bottomed flask equipped with a stir bar was added glucose (4 g) and 40 ml of the aqueous phase, prepared as follows and according to the description in Table 7 below. For Experiment 1, concentrated hydrochloric acid (12 M) was diluted with a 12 M aqueous lithium chloride solution such that the aqueous phase had [H$^+$] and [Li$^+$] as described in Table 7 below. For Experiment 2, hydrochloric acid with concentrations between 4 M and 11 M was diluted with an aqueous lithium chloride solution such that the aqueous phase had [H$^+$] and [Li$^+$] as described in Table 7 below. For Experiment 3, concentrated hydrochloric acid (12 M) was diluted with water such that the aqueous phase had [H$^+$] and [Li$^+$] as described in Table 7 below. For clarity, Experiment 3 had no Li$^+$ in the aqueous phase. For Experiment 4, 10 M hydrochloric acid was diluted with a 10 M aqueous lithium chloride solution such that the aqueous phase had [H$^+$] and [Li$^+$] as described in Table 7 below.

TABLE 7

| Experiment No. | [H$^+$] | [Li$^+$] | [Cl$^-$] | % CMF Yield | % CMF Selectivity |
|---|---|---|---|---|---|
| 1 | 1M | 11M | 12M | 44.1 | 66.9 |
|   | 2M | 10M |   | 59 | 68.6 |

TABLE 7-continued

| Experiment No. | [H+] | [Li+] | [Cl−] | % CMF Yield | % CMF Selectivity |
|---|---|---|---|---|---|
| | 3M | 9M | | 60.5 | 62.8 |
| | 4M | 8M | | 60.6 | 62 |
| | 5M | 7M | | 60.5 | 62.2 |
| | 6M | 6M | | 59.8 | 60.8 |
| | 7M | 5M | | 56.1 | 56.1 |
| | 8M | 4M | | 52.8 | 52.8 |
| | 9M | 3M | | 44.1 | 44.2 |
| | 10M | 2M | | 41 | 41 |
| 2 | 1M | 3M | 4M | 0.3 | 2.8 |
| | 2M | | 5M | 1.5 | 10.7 |
| | 3M | | 6M | 6 | 24.5 |
| | 4M | | 7M | 13.8 | 38.3 |
| | 5M | | 8M | 25.7 | 51.7 |
| | 6M | | 9M | 41.8 | 52.0 |
| | 7M | | 10M | 49.6 | 49.9 |
| | 8M | | 11M | 52.2 | 52.2 |
| | 9M | | 12M | ND | ND |
| | 10M | | 13M | ND | ND |
| 3 | 1M | 0M | 1M | 0 | 0 |
| | 2M | | 2M | 0.3 | 2 |
| | 3M | | 3M | 0.33 | 2.7 |
| | 4M | | 4M | 1.47 | 7 |
| | 5M | | 5M | 3.6 | 14.6 |
| | 6M | | 6M | 8.6 | 24.5 |
| | 7M | | 7M | 21.0 | 35.1 |
| | 8M | | 8M | 32.2 | 36.4 |
| | 9M | | 9M | 44.15 | 44.6 |
| | 10M | | 10M | 37.5 | 37.6 |
| 4 | 4M | 0M | 4M | 1.47 | 7 |
| | | 4M | 8M | 19.71 | 34.98 |
| | | 6M | 10M | 48.17 | 54.98 |
| | | 8M | 12M | 60.6 | 62 |

"ND" means no data was collected for these runs

The mixture was then allowed to stir at room temperature while sealed until all solids were observed to be dissolved into solution. Toluene (80 ml) was then added to the flask. The flask was then sealed and the reaction mixture was stirred for 60 minutes at 110° C. The resulting reaction mixture was then cooled to room temperature. The contents of the flask were then filtered over a 1.6 micron retention glass fiber filter, and the reaction flask and retained solids were washed with 150 ml of toluene in batches. The reaction flask and solids were also washed with water and the resulting aqueous from that wash was diluted for glucose and levulinic acid quantification. The aqueous phase and organic phase were then separated. The recovered aqueous phase was then quantified by volume and samples were taken for CMF, glucose, and levulinic acid quantification. The organic layer was dried over magnesium sulfate, filtered, and diluted for CMF quantification.

Figure 2A:
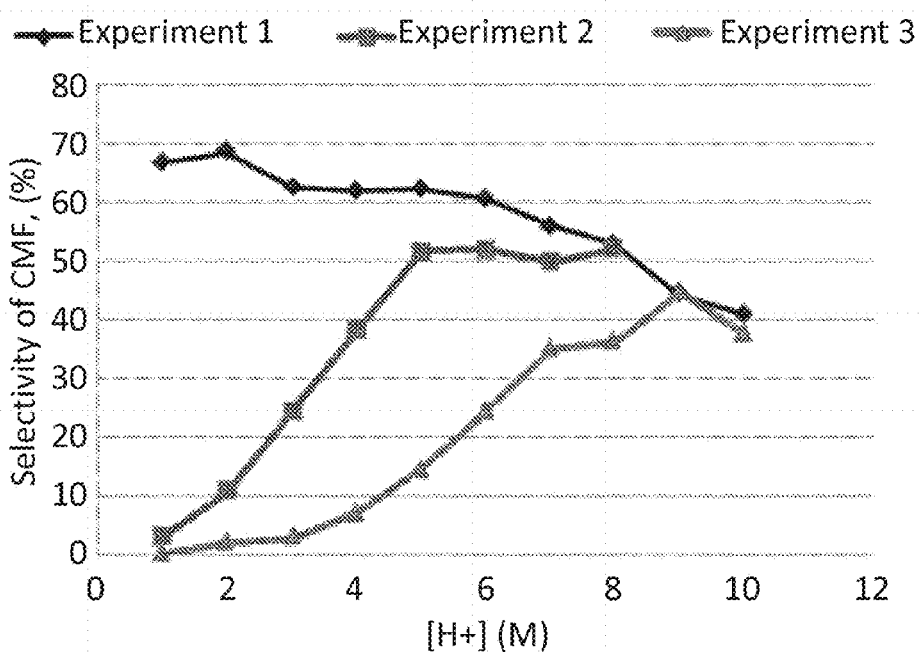
FIG. 2A is a graph comparing the effect of HCl concentration on the selectivity of 5-(chloromethyl)furfural produced.
Figure 2B:
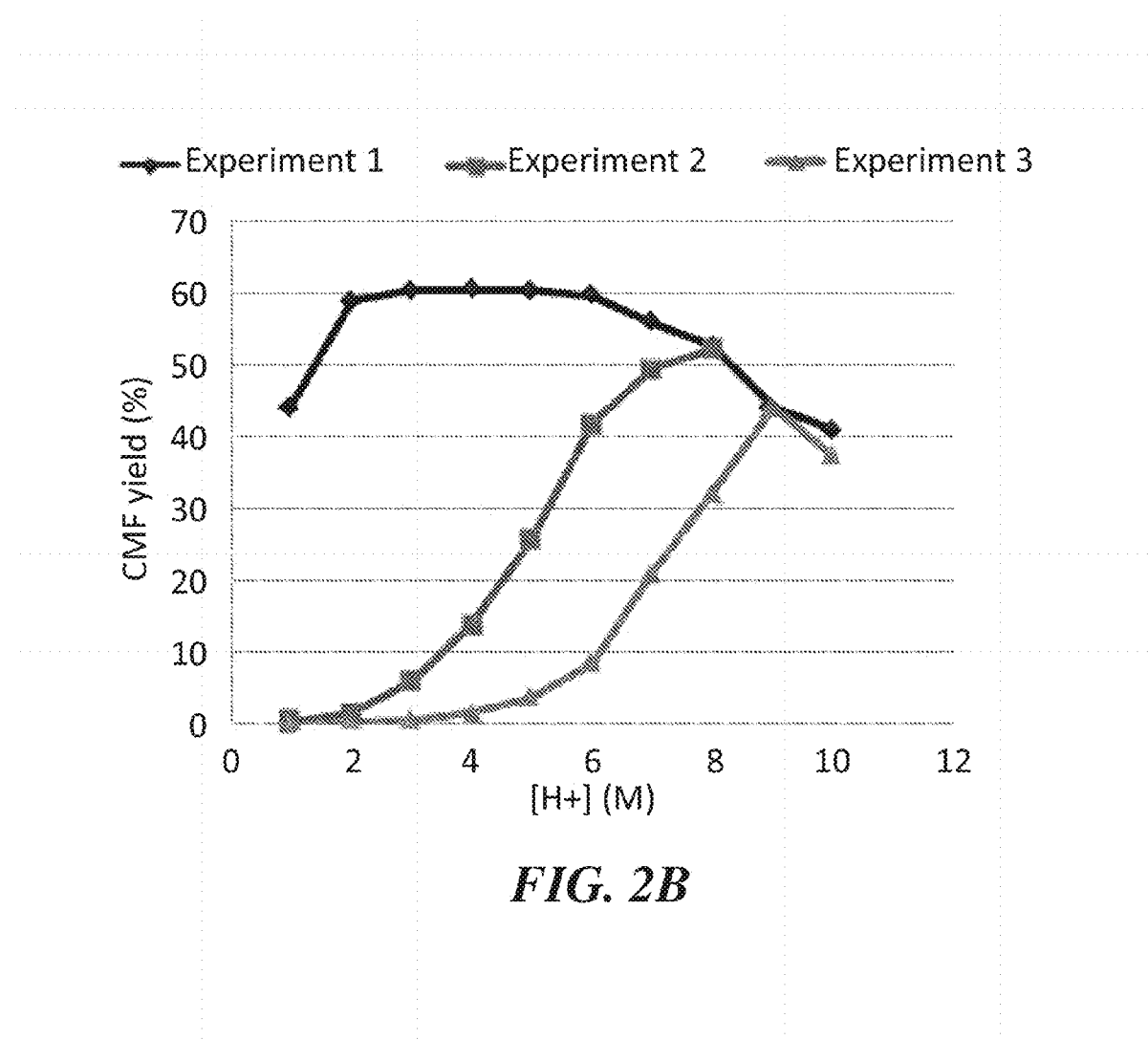
FIG. 2B is a graph comparing the effect of HCl concentration on the yield of 5-(chloromethyl)furfural produced.

Table 7 above summarizes the effect of varying HCl concentration on the yield and selectivity of CMF produced in the reaction. FIGS. 2A and 2B provide graphical representations of the data in Table 7.

Example 6B

Glucose (4000.0 mg) was added to 10 M hydrochloric acid (40 ml) in a 500 ml round bottom flask equipped with a stir bar. Glucose was dissolved by gently stirring at room temperature. Toluene was introduced (80 ml) to the flask creating a biphasic reaction and heated with vigorous stirring in a 110° C. oil bath for 60 minutes. After cooling for 2 minutes until the reaction mixture is at room temperature, the organic phase was decanted. Additional toluene (80 ml) was added and the flask was allowed to stir for 3 minutes and separated. Extraction continued until toluene became clear. The organic phase and toluene extractions were diluted with toluene in a 500 ml volumetric flask. A sample of the contents in the flask was obtained and analyzed by HPLC.

The CMF yield observed was 27.6%; conversion observed was 100.0%; and selectivity observed was 27.6%.

Example 6C

Glucose (4001.0 mg) was added to 12 M hydrochloric acid (40 ml) in a 500 ml round bottom flask equipped with a stir bar. Glucose was dissolved by gently stirring at room temperature. Toluene was introduced (80 ml) to the flask creating a biphasic reaction and heated with vigorous stirring in a 110° C. oil bath for 60 minutes. After cooling for 2 minutes until the reaction mixture is at room temperature, the organic phase was decanted. Additional toluene (80 ml) was added and the flask was allowed to stir for 3 minutes and separated. Extraction continued until toluene became clear. The organic phase and toluene extractions were diluted with toluene in a 500 ml volumetric flask. A sample of the contents in the flask was obtained and analyzed by HPLC.

The CMF yield observed was 32.8%; conversion observed was 100.0%; and selectivity observed was 32.8%.

Example 7

Synthesis of 5-(Chloromethyl)Furfural Using Lithium Triflate and Lithium Chloride as Salts This Example demonstrates the synthesis of CMF using lithium triflate and lithium chloride as the salts.

To a 25 ml volumetric flask was added 23.4 g of lithium triflate and 4.24 g of lithium chloride and deionized water to make a 10 M lithium 4 M chloride 6 M triflate solution. To a 25 ml volumetric flask is added 11.7 M hydrochloric acid (4.3 ml) and 10 M lithium 4 M chloride 6 M triflate solution (20.7 ml). The solution is mixed to make a 2 M hydrogen, 8.3 M lithium, 5.3 M chloride, 5 M triflate solution. The solution was then titrated to confirm hydrogen concentration.

Glucose (2006.8 mg) was added to 20 ml of 2 M hydrogen, 8.3 M lithium, 5.3 M chloride, 5 M triflate solution in a 200 ml heavy-walled round bottom flask equipped with a stir bar. Glucose was dissolved by gently stirring at room temperature for 2 minutes. Toluene was introduced (40 ml) to the flask creating a biphasic reaction and heated with vigorous stirring in a 110 C oil bath for 60 minutes. After cooling for 2 minutes until the reaction mixture is room temperature, the reaction mixture was then filtered, washed with toluene, decanted, and the aqueous was extracted with toluene. The resin was washed with 300 ml of water. The aqueous phase and the resin wash were diluted with water in a 500 ml volumetric flask, the organic phase, toluene wash, and the toluene used for extraction were diluted with Toluene in a 500 ml volumetric flask. A 1 ml aliquot of the organic dilution was diluted with toluene in a 10 ml volumetric flask. A sample of the aqueous dilution, the organic dilution, and the second organic dilution were submitted to HPLC.

The CMF yield observed was 33.2%; conversion observed was 95.3%; and selectivity observed was 34.8%.

Example 8

Synthesis of 5-(Chloromethyl)Furfural Using Magnesium Chloride as Salt

This Example demonstrates the synthesis of CMF using magnesium chloride as the salt.

To a round bottomed flask equipped with stir bar was added 40 mL of the following aqueous solution: 2M [H$^+$], 3.19M [Mg$^{2+}$], 8.43 [Cl$^-$]. Glucose (4 g) was added to the flask and allowed to stir for 10 minutes at room temperature until all of the glucose had visibly dissolved while sealed. Toluene (80 mL) was then added, the flask resealed, and the resulting bi-phase was stirred vigorously for 16 minutes while in a 150° C. oil bath. The flask was then allowed to cool to room temperature. The resulting mixture was filtered, the filtrate was washed with toluene, the biphase was decanted and the organic phase was diluted to 500 ml in toluene for CMF quantification.

The CMF yield was observed to be 18.8%.

Example 9

Synthesis of 5-(Chloromethyl)Furfural Using Calcium Chloride as Salt

This Example demonstrates the synthesis of 5-(chloromethylfurfural) from glucose, hydrochloric acid, and calcium chloride.

A concentrated calcium chloride solution was prepared by diluting 32.78 g of anhydrous calcium chloride to 50 ml in deionized water. The resulting solution was allowed to stir for hours allowing all of the heat to dissipate from the heat of solvation and water was added to make up for any that had evaporated during the mixing time, An aqueous solution was prepared by adding concentrated hydrochloric acid (9 ml, 109.4 mmol Cl-) to the calcium Chloride solution prepared above (41 ml, 549.4 mmol Cl-) for a total of 50 ml of aqueous solution (658.8 mmol Cl-. 13.18 M Cl-). A 40 ml sample of that aqueous solution was then poured into a 500 ml round bottomed flask, and glucose (4.0117 g, 22.27 mmol) was then added and allowed to dissolve into the aqueous solution at room temperature with gentle mixing. Toluene (80 ml) was then added and the reaction vessel was sealed. The vessel was then lowered into a 150° C. oil bath and allowed to stirred for 16 minutes. The reaction mixture was then removed from heat and cooled quickly using an ice water bath.

The reaction mixture was then filtered, and the retained solids were then washed with toluene (200 ml), In a separate flask, the solids were also washed with 200 ml of deionized water. The solids were then dried in an oven, and the aqueous wash was diluted to 250 ml. The organics and aqueous from the first flask were then separated. The aqueous was emptied into a graduated cylinder to determine volume of aqueous recovered and the organics were dried over sodium sulfate, The results of this experiment are summarized below,

| | |
|---|---|
| Glucose In (mg) | 4011.7 |
| Recovered Glucose (mg) | 33.6 |
| % Conversion | 99.16 |
| CMF (mg) | 2133.7 |
| Theoretical CMF (mg) | 3219 |
| % Yield | 66.3 |
| % Selectivity | 66.9 |

Example 10

Synthesis of 5-(Chloromethyl)Furfural Using Corrugated Cardboard as Feedstock

This Example demonstrates the synthesis of CMF from old corrugated cardboard (OCC) as the feedstock.

To a round bottomed flask equipped with stir bar was added 40 mL of the following aqueous solution: 0.7M [H$^+$], 11.4M [Li$^+$], 12M [Cl$^-$]. Shredded corrugated cardboard (4 g) was added to the flask, it was sealed, and allowed to stir for 106 minutes in a 50° C. oil bath. Toluene (80 mL) was then added, the flask resealed, and the resulting bi-phase was stirred vigorously for 20 minutes while in a 155° C. oil bath. The flask was then allowed to cool in an ice bath for 10 minutes. The resulting mixture was vacuum filtered, the filtrate was washed with toluene, the bi-phase was decanted and the organic phase was diluted to 500 mL in toluene for CMF quantification.

The CMF yield observed was 46.9%; conversion observed was 95.5%; and selectivity observed was 49.1%.

Example 11

Synthesis of 5-(Halomethyl)furfurals

This Example demonstrates the synthesis of 5-(chloromethylfurfural) and 5-(bromomehylfurfural) from old corrugated containers (OCC), lithium bromide and hydrochloric acid.

A 12 M lithium bromide solution was prepared by diluting 52.1 g of anhydrous LiBr to 50 ml using deionized water. This solution was then used to dilute 8.5 ml of concentrated hydrochloric acid to 50 ml. To a 500 ml round bottomed flask equipped with a stir bar was added OCC (2.0066 g) and 40 ml of the aqueous prepared above. The flask was then sealed and the mixture was stirred in a 50° C. bath for 60 minutes resulting in a brown liquid phase. Toluene (80 ml) was then added, and the flask was resealed. The resulting bi-phasic solution was then submerged in a 150° C. oil bath and allowed to stir vigorously for 16 minutes. The flask was then quickly cooled to room temperature using an ice water bath.

The contents of the flask were then filtered, and the liquid was deliquored from the produced humin. The solids were then washed with toluene and water, and allowed to dry overnight. The reaction organics and aqueous were separated and the aqueous was washed once with an equal amount of toluene. The combined organics were washed twice with saturated sodium brine solution and the toluene was removed by evaporation. The residual brown oil was then taken up in dichloromethane and quantitatively transferred into a 20 ml scintillation vial and dried via rotoevaporatlon followed by freeze-pump-thaw drying under hi-vac in a diluted argon atmosphere.

The dried product was analyzed by NMR. A mixture of 5-(chloromethylfurfural) and 5-(bromomehylfurfural) were observed in the dried product.

What is claimed is:

1. A method for producing 5-(halomethyl)furfural, comprising:
   a) combining a feedstock, an acid, and a salt in a reaction vessel to form a reaction mixture, wherein:
      the feedstock comprises one or more C6 monosaccharides, disaccharides comprising monomeric units having six carbon atoms, or polysaccharides comprising monomeric units having six carbon atoms:
      the acid is HX, wherein X is halo;
      the salt is A$^{r+}$(X$^-$)$_r$, wherein:
         A$^{r+}$ is a Group I or Group II cation, and
         X$^-$ is a halo anion; and
      the reaction mixture has a [H$^+$] less than or equal to 8 M and a [X$^-$] of at least 8 M; and b) producing 5-(halomethyl)furfural from at least a portion of the feedstock in the reaction mixture.

2. The method of claim 1, wherein X is chloro.

3. The method of claim 1, wherein the acid is added continuously.

4. The method of claim 1, wherein $A^{r+}$ is $Li^+$, $Na^+$, $K^+$, $Rb^+$, $Cs^+$, $Mg^{2+}$, $Ca^{2+}$, or $Sr^{2+}$.

5. The method of claim 4, wherein $A^{r+}$ is $Li^+$.

6. The method of claim 4, wherein $A^{r+}$ is $Ca^{2+}$.

7. The method of claim 1, wherein the reaction mixture has a $[H^+]$ less than or equal to 5 M.

8. The method of claim 1, wherein the reaction mixture has a $[X^-]$ of at least 9 M.

9. The method of claim 1, wherein the reaction mixture has:
a $[H^+]$ less than or equal to 5 M: and
a $[X^-]$ of at least 9 M.

10. The method of claim 1, wherein the reaction mixture has:
a $[H^+]$ less than or equal to 2 M; and
a $[X^-]$ of at least 10 M.

11. The method of claim 1, wherein the 5-(halomethyl)furfural is produced at a temperature of at least 115° C.

12. The method of claim 11, wherein the reaction mixture has a $[H^+]$ less than or equal to 0.6 M.

13. The method of claim 1, wherein the feedstock and the $[H^+]$ is present in the reaction mixture at a molar ratio of 1 : 1.

14. The method of claim 1, wherein the reaction mixture has a $[H^+]$ between the feedstock concentration and 5 M.

15. The method of claim 1, wherein:
the reaction mixture has a $[H^+]$ between the feedstock concentration and 2 M; and
the 5-(halomethyl)furfural is produced at a temperature of at least 135° C.

16. The method of claim 1, wherein the reaction mixture has a $[H^+]$ between 0.1 times the feedstock concentration and 5M.

17. The method of claim 1, wherein the feedstock, the acid and the salt are further combined with a solvent system, wherein the solvent system comprises one or more alkyl phenyl solvents, one or more heavy alkane solvents, one or more ester solvents, one or more aromatic solvents, one or more silicone oils, or any combinations or mixtures thereof.

18. The method of claim 1, wherein the feedstock is selected from the group consisting of corn stover, corn cob, corn kernel, rice flour, whole cane, beet pulp, beet processing raffinate, empty palm fruit bunches, palm fronds, saw dust, wood pellets, rice hulls, peanut hulls, spent grains, paper sludge, cardboard, old corrugated containers (OCC), old newspaper (ONP), mixed paper, wheat straw, paper mill effluent, newsprint, municipal solid wastes, wood chips forest thinnings slash miscanthus, switchgrass, sorghum, bagasse manure, wastewater biosolids, green waste, and food or feed processing residues, or any combinations thereof.

19. The method of claim 1, wherein:
(i) the acid is produced in situ; or
(ii) the salt is produced in situ; or
(ii) both (i) and (ii).

20. The method of claim 1, wherein the reaction mixture has a $[H^+]$ of less than or equal to 2 M.

21. The method of claim 1, wherein the reaction mixture has a $[H^+]$ greater than or equal to 0.0001 M and less than or equal to 8 M.

22. The method of claim 1, wherein the reaction mixture has a $[H^+]$ between 0.25 M and 8 M.

23. The method of claim 1, wherein the reaction mixture has a $[H^+]$ between 0.5 M and 8 M.

24. The method of claim 1, wherein the reaction mixture has a $[H^+]$ between 1 M and 8 M.

25. The method of claim 1, wherein the reaction mixture has a $[H^+]$ between 0.25 M and 5 M.

26. The method of claim 1, wherein the reaction mixture has a $[H^+]$ between 0.5 M and 5 M.

27. The method of claim 1, reaction mixture has a $[H^+]$ between 1 M and 5 M.

28. The method of claim 1, wherein the reaction mixture has a $[H^+]$ between 0.25 M and 2 M.

29. The method of claim 1, wherein the reaction mixture has a $[H^+]$ between 0.5 M and 2 M.

30. The method of claim 1, reaction mixture has a $[X^-]$ of between 8 M and 15 M.

31. The method of claim 1, wherein the feedstock, the acid and the salt are further combined with a solvent system, wherein the solvent system comprises one or more linear alkyl benzenes.

32. The method of claim 1, wherein the feedstock, the acid and the salt are further combined with a solvent system, wherein the solvent system comprises para-xylene, mesitylene, naphthalene, anthracene, toluene, dodecylbenzene, pentylbenzene, hexylbenzene, sulfolane, hexadecane, heptadecane, octadecane, icosane, heneicosane, docosane, tricosane, tetracosane, or any combinations or mixtures thereof.

33. The method of claim 1, wherein the feedstock, the acid and the salt are further combined with a solvent system, wherein the solvent system comprises one or more phenyl ether solvents.

34. The method of claim 1, wherein the feedstock comprises cellulose, glucose, fructose, or any combinations thereof.

35. The method of claim 1, wherein X is bromo.

* * * * *